(12) United States Patent
Valvano et al.

(10) Patent No.: US 11,478,646 B2
(45) Date of Patent: Oct. 25, 2022

(54) METHOD AND APPARATUS FOR MONITORING A PATIENT

(71) Applicants: Jonathan W. Valvano, Austin, TX (US); John A. Pearce, Austin, TX (US); Marc D. Feldman, San Antonio, TX (US); Kaarthik Rajendran, Austin, TX (US); John Porterfield, Austin, TX (US); Anil Kottam, Cedar Park, TX (US); Wes Johnson, Austin, TX (US)

(72) Inventors: Jonathan W. Valvano, Austin, TX (US); John A. Pearce, Austin, TX (US); Marc D. Feldman, San Antonio, TX (US); Kaarthik Rajendran, Austin, TX (US); John Porterfield, Austin, TX (US); Anil Kottam, Cedar Park, TX (US); Wes Johnson, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/316,548

(22) PCT Filed: Jul. 12, 2017

(86) PCT No.: PCT/US2017/041720
§ 371 (c)(1),
(2) Date: Jan. 9, 2019

(87) PCT Pub. No.: WO2018/013694
PCT Pub. Date: Jan. 18, 2018

(65) Prior Publication Data
US 2019/0298997 A1  Oct. 3, 2019

Related U.S. Application Data

(60) Provisional application No. 62/362,416, filed on Jul. 14, 2016.

(51) Int. Cl.
*A61N 1/36* (2006.01)
*A61N 1/365* (2006.01)
(Continued)

(52) U.S. Cl.
CPC ............ *A61N 1/365* (2013.01); *A61B 5/0205* (2013.01); *A61B 5/0538* (2013.01);
(Continued)

(58) Field of Classification Search
CPC ...... A61N 1/365; A61N 1/0595; A61N 1/362; A61N 1/3625; G16H 40/63; A61B 5/0205;
(Continued)

(56) References Cited

U.S. PATENT DOCUMENTS 4,187,854 A * 2/1980 Hepp .................. A61B 5/0006
607/33
6,070,100 A * 5/2000 Bakels ................ A61N 1/3622
607/9

(Continued)

OTHER PUBLICATIONS

Haines DE, Wong W, Canby R, Jewell C, Houmsse M, Pederson D, et al., Validation of a defribriliation lead ventricular volume measurement compared to the three-dimensional echocardiography. Heart Rhythm. Oct. 2017; 14(10): 1515-22.
(Continued)

*Primary Examiner* — Carl H Layno
*Assistant Examiner* — Michael J Lau
(74) *Attorney, Agent, or Firm* — Ansel M. Schwartz

(57) ABSTRACT

An apparatus for monitoring a patient post operation having electrically conducting leads which are adapted to extend from inside the patient. The leads having electrodes adapted to communicate with a heart of the patient and apply electrical signals to the heart. The electrodes providing cardiac signals to the computer in response to the electrical
(Continued)

signals so the computer can determine in real time at least one of heart volume, end diastolic heart volume, end systolic heart volume, stroke volume, change in heart volume, change in stroke volume, contractility, respiration rate or tidal volume regarding the patient.

15 Claims, 18 Drawing Sheets

(51) Int. Cl.
    *G16H 40/63*     (2018.01)
    *A61B 5/0205*     (2006.01)
    *A61B 5/0538*     (2021.01)
    *A61B 5/00*     (2006.01)
    *A61N 1/05*     (2006.01)
    *A61N 1/362*     (2006.01)
    *A61B 5/029*     (2006.01)
    *A61B 5/08*     (2006.01)

(52) U.S. Cl.
    CPC ............ *A61B 5/4836* (2013.01); *A61B 5/686* (2013.01); *A61B 5/7203* (2013.01); *A61N 1/0595* (2013.01); *A61N 1/362* (2013.01); *A61N 1/3625* (2013.01); *G16H 40/63* (2018.01); *A61B 5/029* (2013.01); *A61B 5/0816* (2013.01); *A61B 5/7253* (2013.01); *A61B 5/7257* (2013.01)

(58) Field of Classification Search
    CPC ... A61B 5/0538; A61B 5/4836; A61B 5/7203; A61B 5/029; A61B 5/0816; A61B 5/7253; A61B 5/7257
    USPC .......................................................... 607/9
    See application file for complete search history.

(56) References Cited

U.S. PATENT DOCUMENTS

| | | | |
|---|---|---|---|
| 6,449,509 B1* | 9/2002 | Park | A61N 1/36521 600/533 |
| 6,494,832 B1 | 12/2002 | Feldman et al. | |
| 7,925,335 B2 | 4/2011 | Feldman et al. | |
| 9,295,404 B2 | 3/2016 | Valvano et al. | |
| 9,820,673 B2 | 11/2017 | Feldman et al. | |
| 10,076,669 B2 | 9/2018 | Feldman et al. | |
| 10,376,177 B2 | 8/2019 | Valvano et al. | |
| 10,420,952 B2 | 9/2019 | Feldman et al. | |
| 2002/0082658 A1* | 6/2002 | Heinrich | A61N 1/3918 607/9 |
| 2005/0283213 A1* | 12/2005 | Gray | A61B 90/04 607/115 |
| 2006/0041201 A1* | 2/2006 | Behbehani | A61B 5/4818 600/521 |
| 2006/0100683 A1* | 5/2006 | Yacoubian | A61N 1/0587 607/129 |
| 2006/0155206 A1* | 7/2006 | Lynn | A61B 5/412 600/529 |
| 2008/0194975 A1* | 8/2008 | MacQuarrie | A61B 5/02 600/483 |
| 2008/0269627 A1* | 10/2008 | Cho | A61N 1/3962 600/521 |
| 2010/0168821 A1* | 7/2010 | Johnson | A61B 18/1492 607/63 |
| 2010/0280397 A1* | 11/2010 | Feldman | A61B 5/204 600/486 |
| 2011/0152661 A1 | 6/2011 | Feldman et al. | |
| 2012/0157856 A1* | 6/2012 | An | A61B 5/0538 600/484 |
| 2012/0179382 A1* | 7/2012 | Zhang | A61B 5/02416 702/19 |
| 2012/0203306 A1* | 8/2012 | Sarvazyan | A61N 1/36062 607/61 |
| 2013/0023946 A1* | 1/2013 | Valvano | A61N 1/36125 607/18 |
| 2013/0116681 A1* | 5/2013 | Zhang | A61B 18/1206 606/34 |
| 2014/0018696 A1* | 1/2014 | DeArmond | A61B 5/0538 600/547 |
| 2014/0039333 A1* | 2/2014 | Min | A61B 5/349 600/510 |
| 2014/0100621 A1* | 4/2014 | Feldman | A61B 5/02028 607/4 |
| 2014/0111541 A1* | 4/2014 | Tolkowsky | A61M 25/09 345/632 |
| 2014/0235989 A1* | 8/2014 | Wodlinger | A61B 5/0036 600/374 |
| 2014/0249431 A1* | 9/2014 | Banet | A61B 5/1116 600/485 |
| 2015/0038856 A1* | 2/2015 | Houlton | A61B 5/6826 600/484 |
| 2015/0282758 A1* | 10/2015 | Chang | A61B 5/6823 600/301 |
| 2015/0297099 A1* | 10/2015 | Arad (Abboud) | A61B 5/0205 600/375 |
| 2016/0143543 A1* | 5/2016 | Zhang | A61B 5/316 600/485 |

OTHER PUBLICATIONS

Larson ER, Porterfield JE, Sagar S, Marmol-Velez J, Panday M, Escobedo D, et al. Admittance to detect alterations in left ventricular stroke volume. Heart Rhythm. Jun. 27, 2014; 11(11):2075-83.

Agarwal SK, Wruck L, Quibrera M, Matsushita K, Loehr LR, Chang PP, et al. Temporal Trends in Hospitalization for Acute Decompensated Heart Failure in the United States, 1998-2011. Am J Epidemiol. Mar. 1, 2016; 183(5):462-70.

Stretch R, Sauer CM, Yuh DD, Bonde P. National trends in the utilization of short-term mechanical circulatory support: incidence, outcomes, and cost analysis. J Am Coll Cardiol. Oct. 7, 2014;64(14):1407-15.

Felker GM, O'Connor CM, Braunwald E. Heart Failure Clinical Research Network Investigators. Loop diuretics in acute decompensated heart failure: necessary? Evil? A necessary evil? Circulation: Heart Failure. American Heart Association, Inc.; Jan. 2009;2(1):56-62.

Mandawat A, Rao SV. Percutaneous Mechanical Circulatory Support Devices in Cardiogenic Shock. Circ Cardiovasc Interv. American Heart Association, Inc.; May 2017; 10(5):e004337.

Burkhoff D, Naidu SS. The science behind percutaneous hemodynamic support: a review and comparison of support strategies. Catheter Cardiovasc Interv. Nov. 1, 2012;80(5):816-29.

Fincke R, Hochman JS, Lowe AM, Menon V, Slater JN, Webb JG, et al. Cardiac power is the strongest hemodynamic correlate of mortality in cardiogenic shock: a report from the SHOCK trial registry. J Am Coll Cardiol. Jul. 21, 2004;44(2):340-8.

Torgersen C, Schmittinger CA, Wagner S, Ulmer H, Takala J, Jakob SM, et al. Hemodynamic variables and mortality in cardiogenic shock: a retrospective cohort study. Crit Care. 2009;13(5):R157.

Mendoza DD, Cooper HA, Panza JA. Cardiac power output predicts mortality across a broad spectrum of patients with acute cardiac disease. American Heart Journal. Mar. 2007;153(3):366-70.

Uriel N, Morrison KA, Garan AR, Kato TS, Yuzefpolskaya M, Latif F, et al. Development of a novel echocardiography ramp test for speed optimization and diagnosis of device thrombosis in continuous-flow left ventricular assist devices: the Columbia ramp study. J Am Coll Cardiol. Oct. 30, 2012;60(18):1764-75.

Uriel N, Levin AP, Sayer GT, Mody KP, Thomas SS, Adatya S, et al. Left Ventricular Decompression During Speed Optimization Ramps in Patients Supported by Continuous-Flow Left Ventricular Assist Devices: Device-Specific Performance Characteristics and Impact on Diagnostic Algorithms. J Card Fail. Oct. 2015;21(10):785-91.

Sarkar K, Kini AS. Percutaneous left ventricular support devices. Cardiol Clin. Feb. 2010;28(1);169-84.

(56) References Cited

OTHER PUBLICATIONS

Saffarzadeh A, Bonde P. Options for temporary mechanical circulatory support. J Thorac Dis. Dec. 2015;7(12):2102-11.
Steendijk P. Pressure-volume measurements by conductance catheter during cardiac resynchronization therapy. European Heart Journal Supplements. Aug. 2004;6:D35-42.
Trevino RJ, Jones DL, Escobedo D, Porterfield J, Larson E, Chisolm GB, et al. Validation of a new micro-manometer pressure sensor for cardiovascular measurements in mice. Biomed Instrum Technol. 2010;44(1):75-83.
Krenz M. Conductance, admittance, and hypertonic saline: should we take ventricular volume measurements with a grain of salt: J Appl. Physiol. Dec. 2009;107(6):1683-4.
Raghavan K, Feldman MD, Porterfield JE, Larson ER, Jenkins JT, Escobedo D, et al. A bio-telemetric device for measurement of left ventricular pressure-volume loops using the admittance technique in conscious, ambulatory rats. Physiol Meas. Jun. 2011;32(6):701-15.
Larson ER, Feldman MD, Valvano JW, Pearce JA. Analysis of the spatial sensitivity of conductance/admittance catheter ventricular volume estimation. IEEE Trans Biomed Eng. Aug. 2013;60(8):2316-24.
Porterfield JE, Kottam ATG, Raghavan K, Escobedo D, Jenkins JT, Larson ER, et al. Dynamic correction for parallel conductance, GP, and gain factor, alpha, in invasive murine left ventricular volume measurements. J Appl Physiol. American Physiological Society Bethesda, MD; Dec. 2009;107(6):1693-703.
Hott LM, Oglesby ML, Wang AP, Valvano JW, Feldman MD, A Real-Time Hemodynamic ICD Measurement: Evaluation in Chronically Implanted Canines With Pacing-Induced Dilated Cardiomyopathy, J Am Coll Cardiol EP, vol. 5, No. 6, pp. 742-743, Jun. 2019 PMID: 31221363.
Porterfield JE, Larson ER, Jenkins JT, Escobedo D, Valvano JW, Pearce JA, et al. Left ventricular epicardial admittance measurement for detection of acute LV dilation. J Appl Physiol. Mar. 2011;110(3):799-806.
Kottam ATG, Porterfield J, Raghavan K, Fernandez D, Feldman MD, Valvano JW, et al. Real time pressure-volume loops in mice using complex admittance: measurement and implications. Conf Proc IEEE Eng Med Biol Soc. IEEE; 2006;1:4336-9.
Wei C-L, Valvano JW, Feldman MD, Nahrendorf M, Peshock R, Pearce JA. Volume catheter parallel conductance varies between end-systole and end-diastole. IEEE Trans Biomed Eng. Aug. 2007;54(8):1480-9.
Gabriel S, Lau RW, Gabriel C. The dielectric properties of biological tissues: III. Parametric models for the dielectric spectrum of tissues. Phys Med Biol. Nov. 1996;41(11):2271-93.
K. Ishikawa, Ed., Experimental Models of Cardiovascular Diseases: Methods and Protocols. Humana Press, 2018. pp. 343-352.
Raghavan K, et al., Electrical Conductivity and Permittivity of Murine Myocardium, IEEE Trans. Biomed. Eng., vol. 56, No. 8, pp. 2044-2053, Aug. 2009.

\* cited by examiner

METHOD AND APPARATUS FOR MONITORING A PATIENT

CROSS-REFERENCE TO RELATED APPLICATIONS

This is a 371 application of PCT application number PCT/US2017/041720 filed Jul. 12, 2017, which claims priority from U.S. provisional application Ser. No. 62/362,416 filed Jul. 14, 2016, all of which are incorporated by reference herein.

FIELD OF THE INVENTION

The present invention is related to using information with a post-surgical patient in regard to leads that extend from the patient's chest after the chest has been closed. (As used herein, references to the "present invention" or "invention" relate to exemplary embodiments and not necessarily to every embodiment encompassed by the appended claims.) More specifically, the present invention is related to using admittance information with a post-surgical patient in regard to leads that extend from the patient's chest after the chest has been closed.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Standard care for open heart surgery is to place two or more temporary pacing wires into the heart. These wires are used to pace the heart if the patient heart rhythm needs adjustment. Often these wires go unused. One embodiment of the present invention attaches to these temporary pacing wires to make cardiac measurements. A low and safe current is injected from one pacing wire to another. The frequency of this current is high enough and the amplitude is low enough that this current does not damage or stimulate the heart. Voltage is measured on these electrodes or on other nearby electrodes also placed on the heart. The voltage and current data are combined to derive electrical admittance. Prior art allows for the derivation of cardiac function from these electrical measurements, such as heart rate, left ventricular end diastolic volume, left ventricular end systolic volume, left ventricular stroke volume and ejection fraction. However, herein are presented techniques to remove respiratory and motion artifacts, improving the signal to noise ratio. It is critical that complex electrical properties be measured so the contribution of the myocardial muscle can be removed, resulting in a signal sensitive to the volume of blood in the heart. The availability of such a device will allow for continuous monitoring of cardiac function during the post-surgical recovery.

One example of how this would work in post-surgical applications, suppose a patient who has undergone an open heart surgery decompensates in the hospital the day after his/her surgery. The treating physician would have two potential treatments for this emergency situation that are opposite in nature. If the heart is weaker (low contractility, normal EDV, higher ESV than normal, lower SV than normal), then the treatment is to give a positive inotrope (this raises pressure, and blood flow in hearts that have enough blood). If instead the patient is decompensating because of low volume, (low EDV, but normal contractility, normal ESV, potentially lower SV) then the treatment is to give more fluids like IV saline. Choosing the wrong treatment can lead to further decompensation of the patient, and these decisions are often made somewhat uninformed, because of the lack of hemodynamic information.

It is important to note that the electrodes being used in this invention are normally only used for ECG measurement, and pacing in emergency situations, such as when heart block occurs due to the surgical intervention the patient is recovering from. Currently, if a doctor needs to know more about the volume status (or hemodynamic status) of the patient to determine correct treatment, a Swan Ganz, or other pressure/flow measurement intervention must be performed. Usually this involves a consult with an interventional cardiologist. In the situation where the present invention is used, the time necessary for this procedure, the extra interventional cardiologist, and the associated risks of additional catheterization in a weak heart can be avoided.

BRIEF SUMMARY OF THE INVENTION

The present invention is a bedside monitor that measures cardiac and pulmonary function using electrical impedance and electrical admittance in, on, and across the heart. Electrical impedance (Z) is the ratio of the effort divided by flow as electrical energy flows through an object. Electrical admittance (Y) is the ratio of flow divided by effort. The impedance and admittance of living tissue are complex numbers; this means electrical energy is both reduced in amplitude and delayed in time (phase shift) by the tissue during transfer. Prior art has defined the electrodes and the relationship between electrical properties and heart physiology. Prior art also defined method that provides accurate measurements that are both low power and small in size.

Herein is presented in substantial detail several possible embodiments of a method and apparatus, based on complex measurements of electrical admittance, which will allow for monitoring of cardiac and pulmonary functions. First, prior art describes how to perform admittance measurements from standard pacemaker leads. The signal processing techniques presented here significantly improves signal to noise ratio when measurements are taken within the pacemaker while the patient is ambulatory. A second scenario for this method and apparatus is for a bedside monitor for patients with temporary pacing wires.

A first embodiment is to incorporate the method and apparatus [19-24] to pacemakers and AICDs, using currently deployed bi-ventricular and AICD leads, to electrically detect either true LV preload, or an increase in LV preload from baseline. Bi-ventricular and the RV AICD leads are already located in the ideal locations—the lateral LV epicardium and the right ventricular (RV) septum. Since blood has 5-fold higher conductivity than myocardium, the preferential path for a substantial fraction of the current flow will be the LV blood volume. This low-power admittance device can be "piggy-backed" onto implanted AICD and bi-ventricular pacemakers to serve as an early warning system for impending heart failure. Piggy-backed means one can take an existing pacemaker design and add this device to it, without major redesign of the pacemaker itself. This means the admittance circuits need not be included in one of the internal pacemaker chips; rather it could be added to the system without redesigning the pacemaker circuits themselves. In particular, the device uses the same catheters, the same communication channel, and the same power source as the pacemaker. The device can be triggered by the pacemaker or it can run untriggered (i.e., it runs periodically). The output of the device will be a true/false warning signal, or a quantitative measure of heart volume. In this configuration, the inventive device does not alter how the pacemaker operates.

A second embodiment of the method and apparatus is for post-surgical monitoring. Standard care for open heart surgery is to place two or more temporary pacing wires into the heart. These wires are used to pace the heart if the patient heart rhythm needs adjustment. Often these wires go unused. One embodiment of the present invention attaches to these temporary pacing wires to make cardiac measurements. A low and safe current is injected from one pacing wire to another. The frequency of this current is high enough and the amplitude is low enough that this current does not damage or stimulate the heart. Voltage is measured on these electrodes or on other nearby electrodes also placed on the heart. The voltage and current data are combined to derive electrical admittance. Prior art allows for the derivation of cardiac function from these electrical measurements, such as heart rate, left ventricular end diastolic volume, left ventricular end systolic volume, left ventricular stroke volume and ejection fraction. However, herein is presented methods to remove respiratory and motion artifacts, improving the signal to noise ratio. It is critical that complex electrical properties be measured so the contribution of the myocardial muscle can be removed, resulting in a signal sensitive to the volume of blood in the heart. The availability of such an apparatus will allow for continuous monitoring of cardiac function during the post-surgical recovery.

The present invention pertains to an apparatus for monitoring a patient post operation. The apparatus comprises a computer disposed external to the patient. The apparatus comprises a stimulator for producing electrical signals. The apparatus comprises electrically conducting leads in communication with the computer which are adapted to extend from inside the patient. The leads having electrodes adapted to communicate with a heart of the patient and apply the electrical signals to the heart. The electrodes providing cardiac signals to the computer in response to the electrical signals so the computer can determine in real time at least one of heart volume, end diastolic heart volume, end systolic heart volume, stroke volume, change in heart volume, change in stroke volume, contractility, respiration rate or tidal volume regarding the patient.

The present invention pertains to a method for monitoring a patient post operation. The method comprises the steps of providing cardiac signals to a computer disposed external to the patient from electrically conducting leads in communication with the computer which extend from inside the patient, the leads having a plurality of electrodes adapted to contact a heart of the patient. There is the step of determining with the computer from the cardiac signals in real time at least one of heart volume, end diastolic heart volume, end systolic heart volume, stroke volume, change in heart volume, change in stroke volume, contractility, respiration rate or tidal volume regarding the patient.

The present invention pertains to an apparatus for monitoring a heart of a patient. The apparatus comprises a computer. The apparatus comprises electrodes in communication with the heart. The electrodes providing cardiac signals to the computer from which the computer determines attributes of the heart. The computer separating cardiac, respiratory and motion components from the cardiac signals.

The present invention pertains to a method for monitoring a heart of a patient. The method comprises the steps of providing cardiac signals to a computer from which the computer determines attributes of the heart from electrodes in communication with the heart. There may be the step of separating cardiac, respiratory and motion components by the computer from the cardiac signals.

The present invention pertains to an apparatus for monitoring a patient. The apparatus comprises a computer. The apparatus comprises a switch in communication with the computer and controlled by the computer. The apparatus comprises a first electrode adapted to be in communication with a muscle of the patient and in communication with the switch. The apparatus comprises a second electrode adapted to be in communication with the muscle of the patient and in communication with the switch. The apparatus comprises a third electrode adapted to be in communication with the muscle of the patient and in communication with the switch. The apparatus comprises a fourth electrode adapted to be in communication with the muscle of the patient and in communication with the switch. The computer choosing which of the second, third or fourth electrodes to which the first electrode will deliver current to create a first vector having an associated muscle signal which is received by the computer for the computer to measure admittance regarding the muscle.

The present invention pertains to a method for monitoring a patient. The method comprises the steps of a computer controlling and changing with a switch in communication with the computer which pairs of electrodes of a plurality of electrodes in communication with a heart of the patient to produce a plurality of vectors each having associated cardiac signals at a given time. There is the step of determining with the computer at least one of heart volume, end diastolic heart volume, end systolic heart volume, stroke volume, change in heart volume, change in stroke volume, contractility, respiration rate or tidal volume regarding the patient using admittance from the cardiac signals of each vector.

In summary, a technique and an apparatus has been developed, which uses existing electrodes placed on or around the heart that is capable of measuring heart volume, change in heart volume, and/or stroke volume.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 1A:
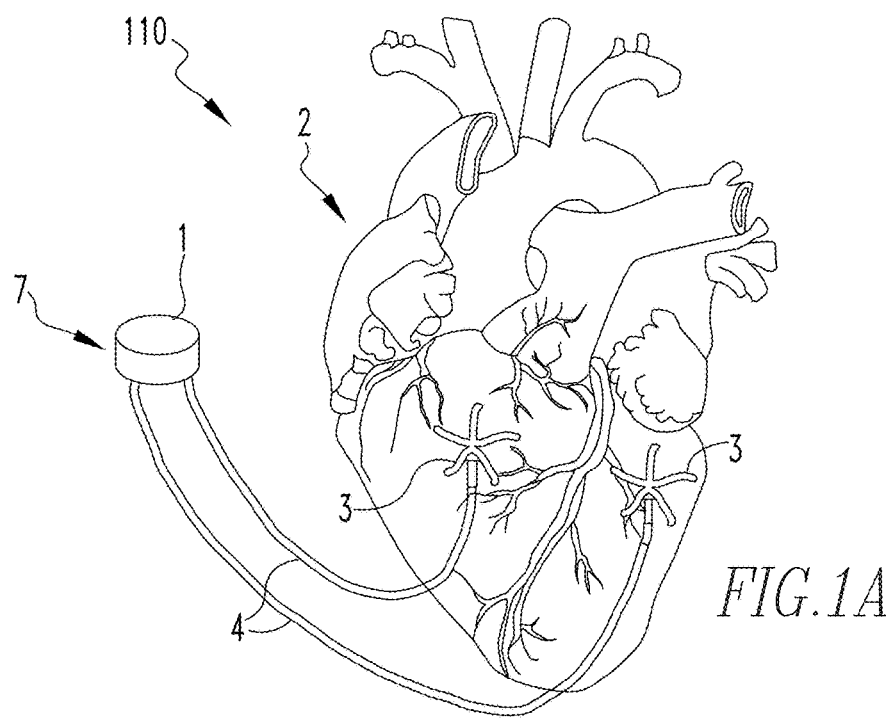
FIGS. 1A and 1B show a basic idea of the Bedside Cardiac Monitor used to measure cardiac and pulmonary function. Two or more electrodes placed in or around the heart using one or more pacing wires.
Figure 1B:
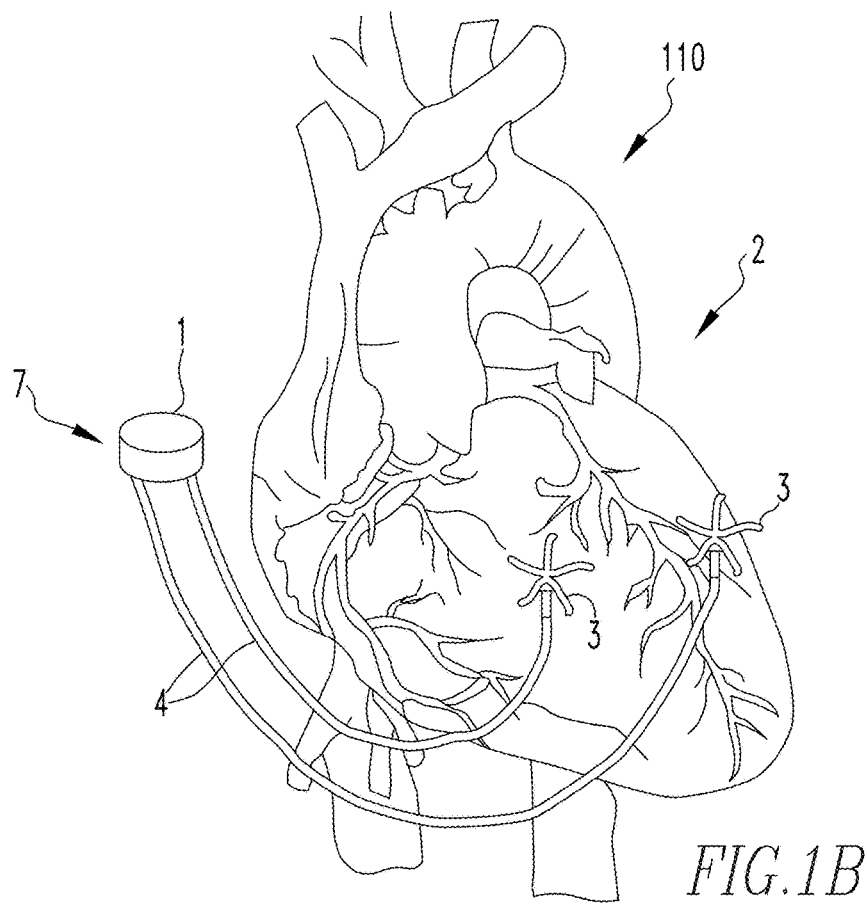

Referring now to the drawings wherein like reference numerals refer to similar or identical parts throughout the several views, and more specifically to FIGS. 1A, 1B, 2, 3A-3F, 4 and 5 thereof, there is shown an apparatus 110 for monitoring a patient post operation. The apparatus 110 comprises a computer 29 disposed external to the patient. The apparatus 110 comprises a stimulator 112 for producing electrical signals. The apparatus 110 comprises electrically conducting leads 25 in communication with the computer 29 which are adapted to extend from inside the patient. The leads 25 having electrodes 3 adapted to communicate with a heart 2 of the patient and apply the electrical signals to the heart 2. The electrodes 3 providing cardiac signals to the computer 29 in response to the electrical signals so the computer 29 can determine in real time at least one of heart volume, end diastolic heart volume, end systolic heart volume, stroke volume, change in heart volume, change in stroke volume, contractility, respiration rate or tidal volume regarding the patient.

Figure 20:
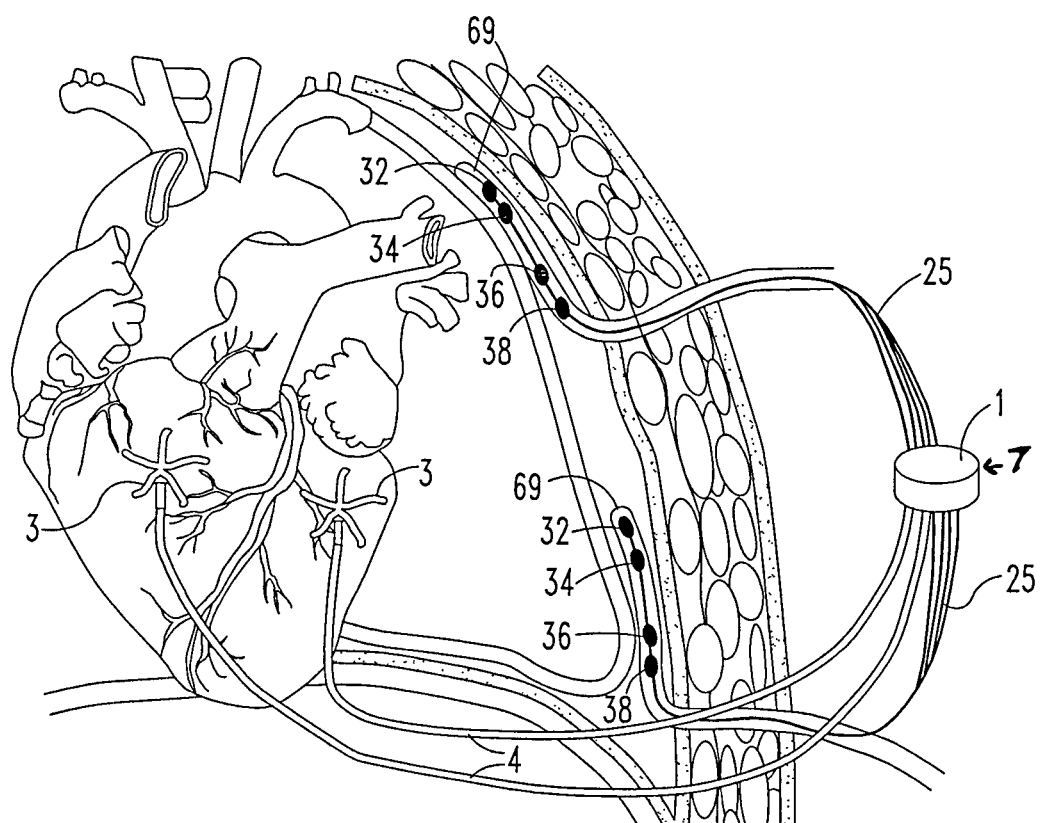
FIG. 20 shows tubes with electrodes as well as electrodes attached to the heart.
Figure 21:
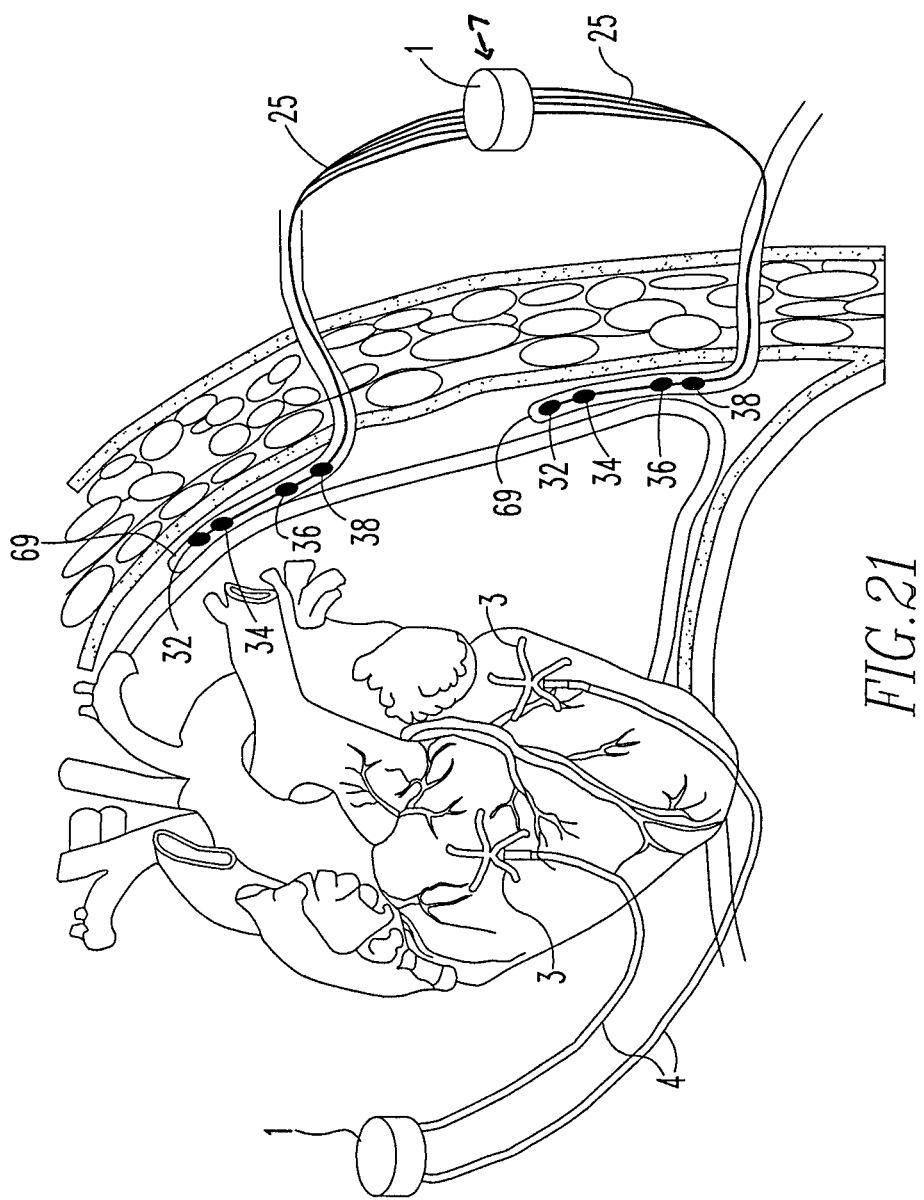
FIG. 21 shows tubes with electrodes as well as electrodes attached to the heart and two external pacemakers.

The computer 29 may determine in real time and continuously using admittance the at least one of heart volume, end diastolic heart volume, end systolic heart volume, stroke volume, change in heart volume, change in stroke volume, contractility, respiration rate or tidal volume regarding the patient. The computer 29 and the stimulator 112 may be disposed in and part of an external pacemaker 7 which can electrically stimulate the electrodes 3 and pace the heart 2. The leads 25 may be pacing leads 25 with the electrodes 3 that pace the heart 2 from the pacemaker 7, or leads 25 with the electrodes 3 placed on one or more chest tubes 69 which extend from the patient and are disposed adjacent the heart 2 of the patient, as shown in FIGS. 20 and 21. FIG. 20 shows all the pacing wires from all the electrodes 3 connect with a single pacemaker 7 having the admittance device. FIG. 21 shows two distinct and separate pacemakers 7, each having its own admittance device. In FIG. 21 the electrodes 3 on the tubes 69 connect with one of the pacemakers 7 and the sewn in electrodes 3 connect with the other pacemakers. The chest tubes 69 are placed around the heart 2 within the heart 2 and pericardial space. Each chest tube would have multiple electrodes 3 embedded in the plastic and could interact with electrodes 3 sewn into the heart 2 as backup pacing wires, or serve as independent electrodes 3 without interaction with the pacing electrodes 3. The electrodes 3 with the tubes 69 operate the same way as described herein for the electrodes 3 that are attached or sewn to the heart 2. Both the chest tubes 69 and pacing wires are all placed routinely after open heart surgery.

Figure 8:
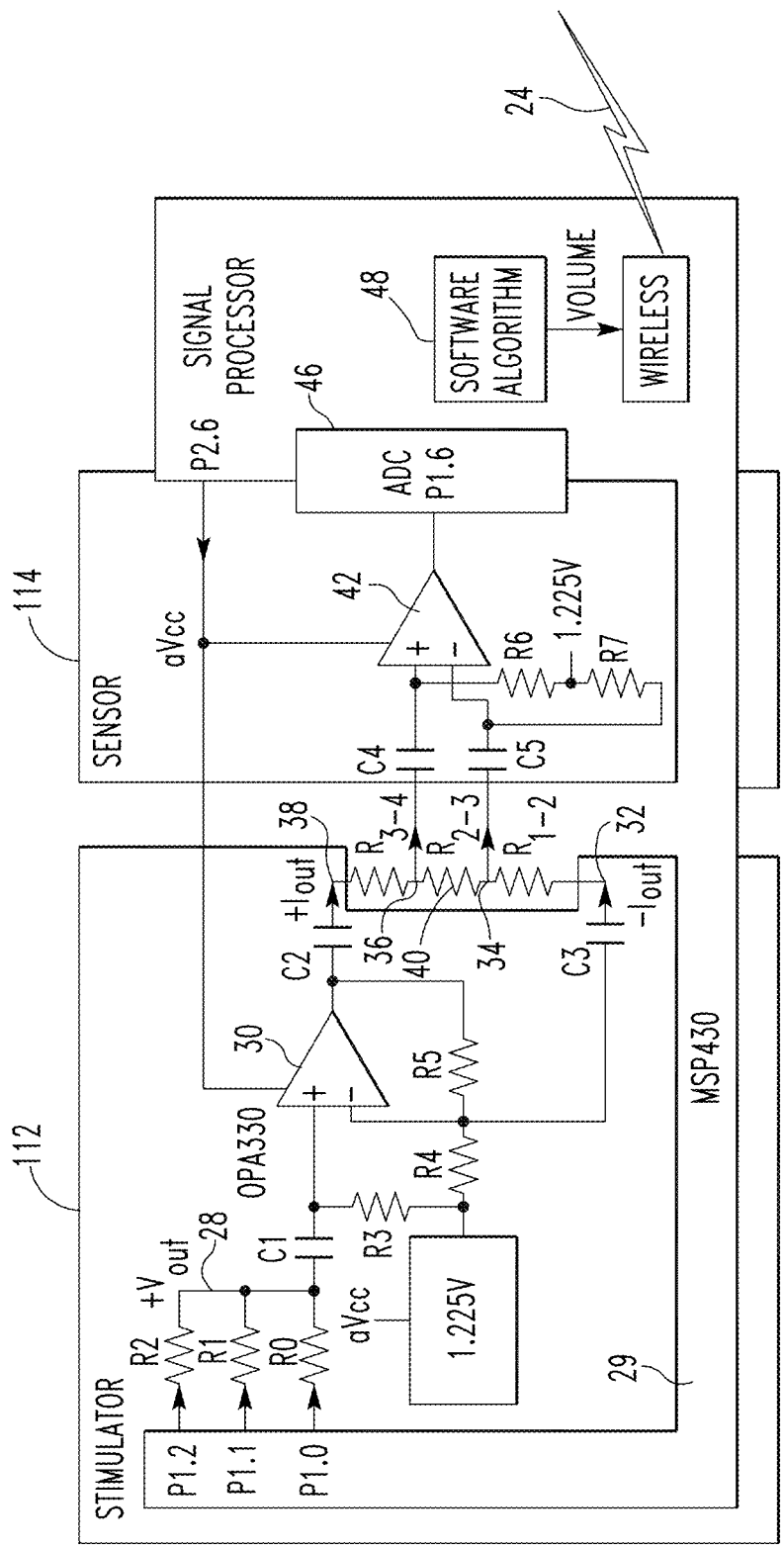
FIG. 8 shows a prototype circuit with stimulator, sensor and signal processor.

The pacing leads 25 may be either unipolar pacing wires 11 each having one electrode, bipolar pacing wires 11 having to pacing wires, or quadrupole pacing wires 12 each having four pacing wires, as shown in FIGS. 3A-3F. There may be at least four electrodes 3 where a first two of the electrodes 3 conduct current and a second two electrodes 3 receive voltage resulting from the current from the first two electrodes 3. The apparatus 110 may include a SinDac 28 disposed in the pacemaker 7 which generates a sine wave at a specific frequency in regard to the current, as shown in FIG. 8.

Figure 9:
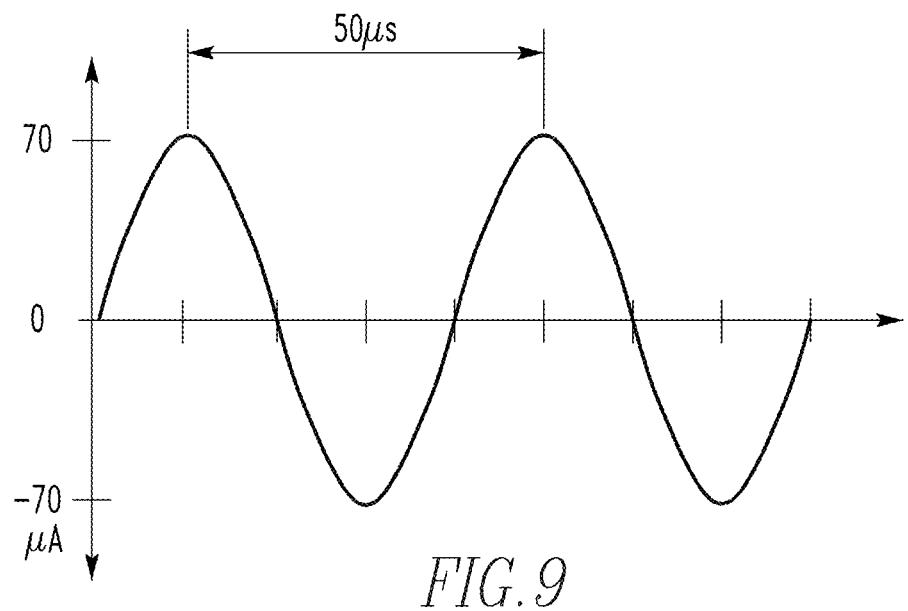
FIG. 9 shows an example 20 kHz current stimulus.
Figure 10:
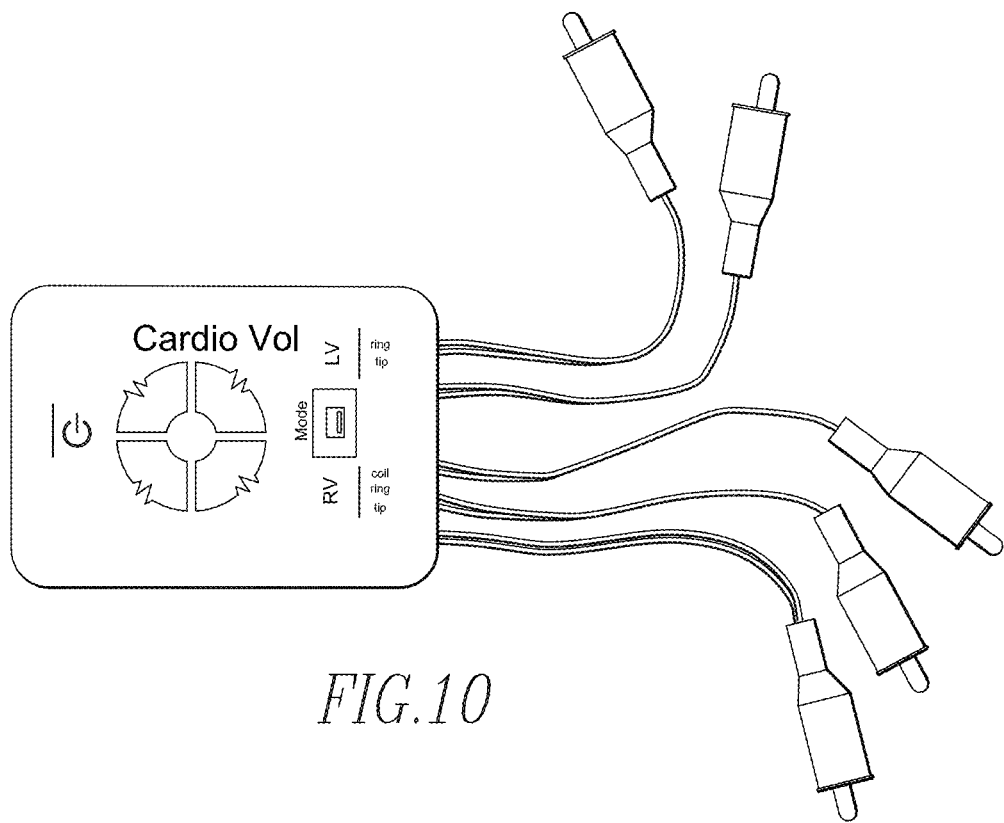
FIG. 10 shows a CardioVol device used to measure cardiac and pulmonary function.
Figure 11:
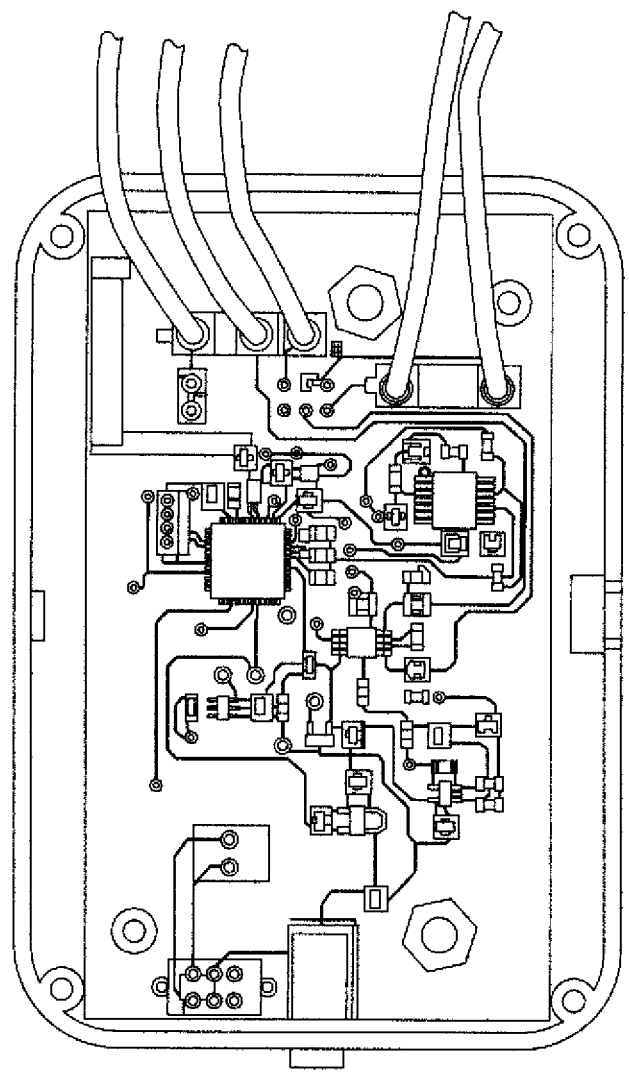
FIG. 11 shows a CardioVol PCB used to measure cardiac and pulmonary function.

The apparatus 110 may include a sensor 114, a signal processor 116 of the computer 29 and a low-power circuit 30; where an average current to operate the sensor 114, stimulator 112 and signal processor 116 is less than 14 mA, and the low-power circuit 30 is used to deliver the current to the current electrodes 3, as shown in FIGS. 9-11. The apparatus 110 may include a low-power amplifier 42 and ADC 46 used to collect voltage signals for the computer 29 to use for analysis. The computer 29 may separate cardiac, respiratory and motion components from the cardiac signals. The apparatus 110 may include a switch 58 in communication with the computer 29 that controls and changes which pairs of electrodes 3 of the plurality of electrodes 3 produce the cardiac signals at a given time.

The present invention pertains to a method for monitoring a patient post operation. The method comprises the steps of providing cardiac signals to a computer 29 disposed external to the patient from electrically conducting leads 25 in communication with the computer 29 which extend from inside the patient, the leads 25 having a plurality of electrodes 3 adapted to contact a heart 2 of the patient. There is the step of determining with the computer 29 from the cardiac signals in real time at least one of heart volume, end diastolic heart volume, end systolic heart volume, stroke volume, change in heart volume, change in stroke volume, contractility, respiration rate or tidal volume regarding the patient.

There may be the steps of placing the plurality of electrodes 3 in contact with the heart 2, externalizing electrical leads 25 extending from the electrodes 3 with respect to the patient, and connecting the leads 25 to the computer 29. The determining step may include the step of the computer 29 determining in real time and continuously the at least one of heart volume, end diastolic heart volume, end systolic heart volume, stroke volume, change in heart volume, change in stroke volume, contractility, respiration rate or tidal volume regarding the patient using admittance associated with the heart 2. There may be the step of providing current signals from a stimulator 112 to the electrodes 3 to generate the cardiac signals.

The computer 29 and the stimulator 112 may be disposed in and part of an external pacemaker 7 which can electrically stimulate the electrodes 3 and pace the heart 2. The leads 25 may be pacing leads 25 with the electrodes 3 that pace the heart 2 from the pacemaker 7. There may be at least four electrodes 3, and there may be the steps of a first two of the electrodes 3 conducting current and a second two electrodes 3 receiving voltage resulting from the current from the first two electrodes 3. There may be the step of a SinDac 28 disposed in the pacemaker 7 generating a sine wave at a specific frequency in regard to the current.

There may be the step of the computer 29 separating cardiac, respiratory and motion components from the cardiac signals. There may be the step of a switch 58 in communication with the computer 29 controlling and changing which pairs of electrodes 3 of the plurality of electrodes 3 produce the cardiac signals at a given time.

The present invention pertains to an apparatus 110 for monitoring a heart 2 of a patient. The apparatus 110 comprises a computer 29. The apparatus 110 comprises electrodes 3 in communication with the heart 2. The electrodes 3 providing cardiac signals to the computer 29 from which the computer 29 determines attributes of the heart 2. The computer 29 separating cardiac, respiratory and motion components from the cardiac signals. See FIGS. 12-16.

The apparatus 110 may include an EKG channel in which the computer 29 measures heart 2 rate. The computer 29 synchronizes admittance signals associated with the cardiac signals to the heart rate and then filters the admittance signal so respiratory and motion artifacts are removed. The computer 29 may collect admittance data of the heart 2 over a window of time T. The computer 29 may perform a Fast Fourier Transform on the admittance data collected in the window.

The computer 29 may select frequency components in regard to the admittance data on which the computer 29 has performed the Fast Fourier Transform. The computer 29 may perform an inverse Fast Fourier Transform to re-create cardiac signals from the heart 2. The computer 29 may perform a root mean squared calculation on the cardiac signal as a measure of left ventricular stroke volume, where a maximum signal of the calculation is related to diastolic volume and a minimum signal of the calculation is related to systolic volume.

The present invention pertains to a method for monitoring a heart 2 of a patient. The method comprises the steps of providing cardiac signals to a computer 29 from which the computer 29 determines attributes of the heart 2 from electrodes 3 in communication with the heart 2. There may be the step of separating cardiac, respiratory and motion components by the computer 29 from the cardiac signals.

There may be the steps of measuring with the computer 29 a heart rate of the patient, synchronizing admittance signals associated with the cardiac signals by the computer 29 to the heart rate of the patient and filtering the admittance signal so respiratory and motion artifacts are removed by the computer 29. There may be the step of the computer 29 collecting admittance data of the heart 2 over a window of time T. There may be the step of the computer 29 performing a Fast Fourier Transform on the admittance data collected in the window.

There may be the step of selecting with the computer 29 frequency components in regard to the admittance data on which the computer 29 has performed the Fast Fourier Transform. There may be the step of the computer 29 performing an inverse Fast Fourier Transform to re-create cardiac signals from the heart 2. There may be the step of the computer 29 performing a root mean squared calculation on the cardiac signal as a measure of left ventricular stroke volume, where a maximum signal of the calculation is related to diastolic volume and a minimum signal of the calculation is related to systolic volume.

Figure 17:
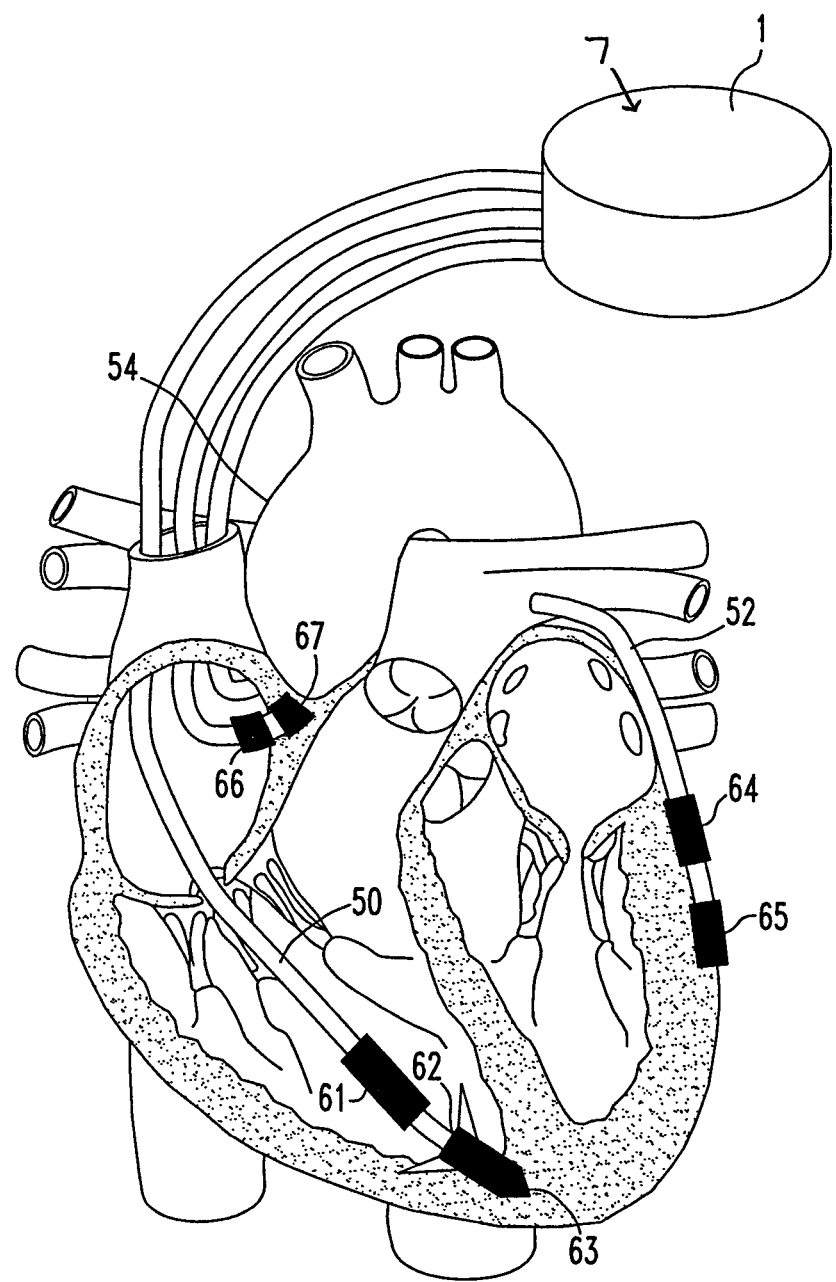
FIG. 17 shows a heart with three pacemaker leads.
Figure 18:
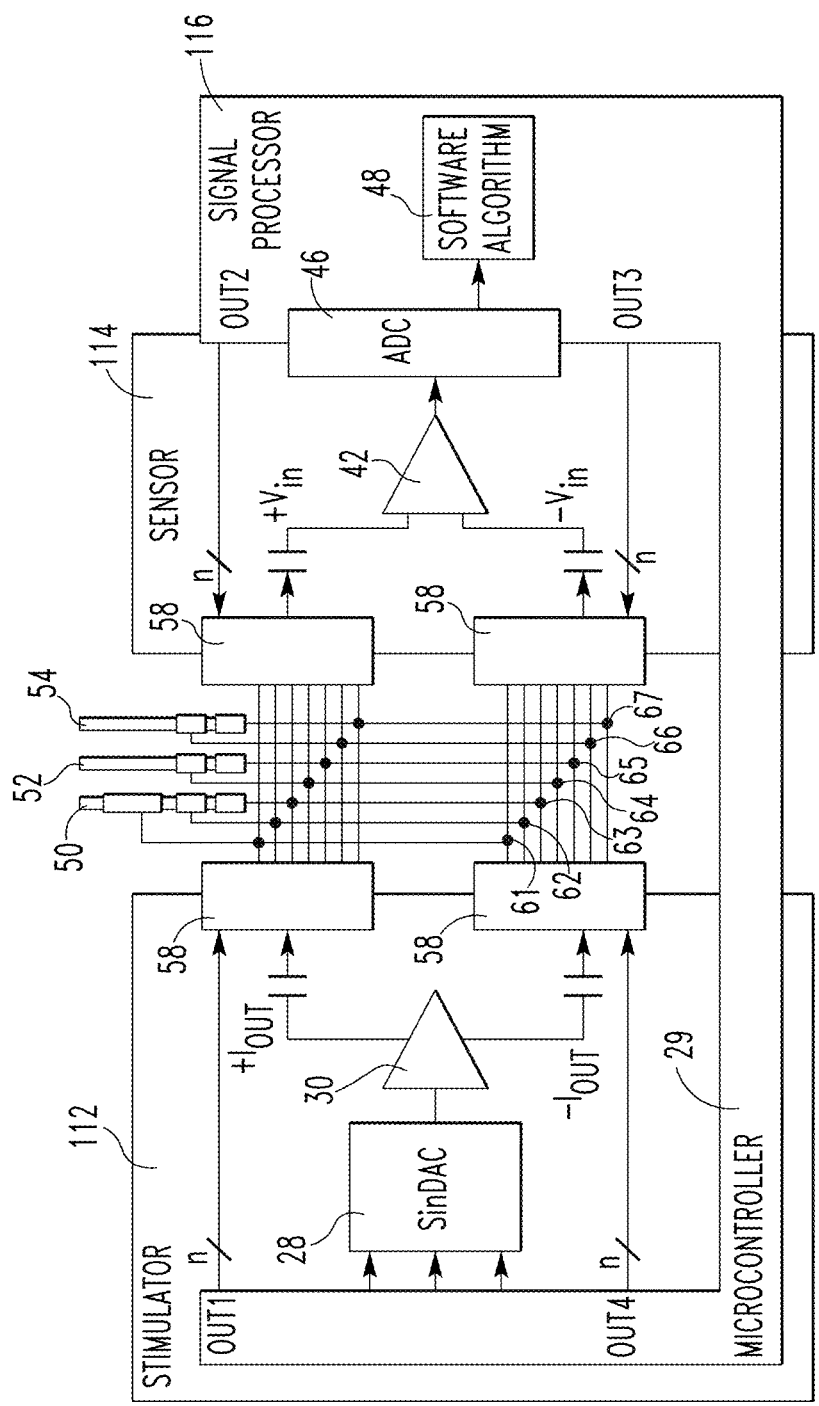
FIG. 18 shows a device with 4 banks of analog switches used to collect multivector signals.
Figure 19:
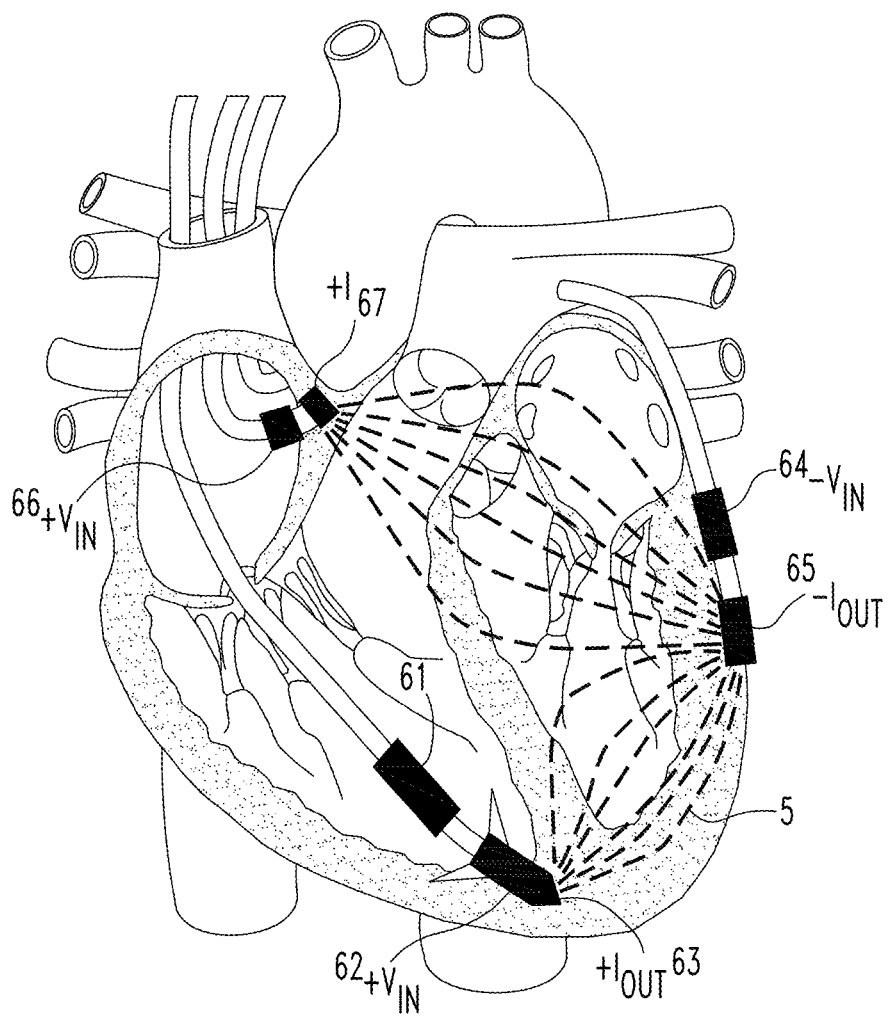
FIG. 19 shows hexapolar measurement using 6 electrodes to measure LV volume.

The present invention pertains to an apparatus 110 for monitoring a patient, as shown in FIGS. 17-19. The apparatus 110 comprises a computer 29. The apparatus 110 comprises a switch 58 in communication with the computer 29 and controlled by the computer 29. The apparatus 110 comprises a first electrode 32 adapted to be in communication with a muscle of the patient and in communication with the switch 58. The apparatus 110 comprises a second electrode 34 adapted to be in communication with the muscle of the patient and in communication with the switch 58. The apparatus 110 comprises a third electrode 36 adapted to be in communication with the muscle of the patient and in communication with the switch 58. The apparatus 110 comprises a fourth electrode 38 adapted to be in communication with the muscle of the patient and in communication with the switch 58. The computer 29 choosing which of the second, third or fourth electrodes 34, 36, 38 to which the first electrode 32 will deliver current to create a first vector having an associated muscle signal which is received by the computer 29 for the computer 29 to measure admittance regarding the muscle.

The computer 29 may choose the first electrode 32 to deliver current to the second electrode 34 to generate a first vector having a muscle signal from the second electrode 34, and then the computer 29 may choose the first electrode 32 to deliver current to the third electrode 36 to generate a second vector having a muscle signal from the third electrode 36. The computer 29 may calculate an associated admittance for each vector from each vector's associated muscle signal. The switch 58 may include a plurality of banks of analog switches that are controlled by the computer 29. The banks of switches in electrical communication with the electrodes 3.

The computer 29 may activate at least two of the banks of switches at a same time so current is directed to multiple electrodes 3 at the same time to create multiple vectors and the computer 29 averages together voltages from muscle signals associated with different vectors from the same time. The apparatus 110 may include a sensor 114 which includes two of the plurality of banks of analog switches used to select multiple admittance vectors, a low-power amplifier 42 connected to the two banks of switches. The low-power amplifier 42 connected to an ADC 46 of a signal processor 116 of the computer 29. The computer 29 having a software algorithm to measure heart volume from electrical property measurement associated with the vectors.

The first electrode 32 may be adapted to be in contact with the muscle of the patient or on a chest tube extending from the patient and disposed adjacent the muscle and in communication with the muscle. The second electrode 34 may be adapted to be in contact with the muscle of the patient or on the chest tube or on another chest tube and in communication with the muscle. The third electrode 36 may be adapted to be in contact with the muscle of the patient or on the chest tube or the other chest tube in communication with the muscle. The fourth electrode 38 may be adapted to be in contact with the muscle of the patient or on the chest tube or the other chest tube and in communication with the muscle.

The present invention pertains to a method for monitoring a patient. The method comprises the steps of a computer 29 controlling and changing with a switch 58 in communication with the computer 29 which pairs of electrodes 3 of a plurality of electrodes 3 in communication with a heart 2 of the patient to produce a plurality of vectors each having associated cardiac signals at a given time. There is the step of determining with the computer 29 at least one of heart volume, end diastolic heart volume, end systolic heart volume, stroke volume, change in heart volume, change in stroke volume, contractility, respiration rate or tidal volume regarding the patient using admittance from the cardiac signals of each vector.

There may be the steps of the computer 29 choosing a first electrode 32 to deliver current to a second electrode 34 to generate a first vector having a cardiac signal from the second electrode 34, and then the computer 29 choosing the first electrode 32 to deliver current to a third electrode 36 to generate a second vector having a cardiac signal from the third electrode 36. There may be the step of the computer 29 calculating an associated admittance for each vector from each vector's associated cardiac signal. The switch 58 may include a plurality of banks of analog switches and including the step of the computer 29 controlling the banks of switches, the banks of switches in electrical communication with the electrodes 3.

There may be the step of the computer 29 activating at least two of the banks of switches at a same time so current is directed to multiple electrodes 3 at the same time to create multiple vectors and the computer 29 averages together voltages from cardiac signals associated with different vectors from the same time. There may be a sensor 114 which includes two of the plurality of banks of analog switches used to select multiple admittance vectors, a low-power amplifier 42 connected to the two banks of switches. The low-power amplifier 42 connected to an ADC 46 of a signal processor 116 of the computer 29. The computer 29 may have a software algorithm for measuring heart volume from electrical property measurement associated with the vectors.

FIGURES—REFERENCE NUMERALS

1—Admittance device
2—Heart
3—Tip of the cardiac pacing wire (electrodes)
4—Cardiac pacing wire
5—Paths as current flows between one electrode and another
7—Pacemaker
10—Exposed contact area for a unipolar electrode pacing wire
11—Exposed contact areas for a bipolar electrode pacing wire
12—Exposed contact areas for a quadripolar electrode pacing wire
20—Right ventricle
22—Left ventricle
24—Wireless ink
25—Lead wires between electrodes and device
26—Apparatus to mount electrodes on the skin surface
27—Four or more electrodes making electrical contact with the skin
28—One or more SinDACs used to create a sine wave at a specific frequency
29—Microcontroller
30—Voltage to current circuit applying current to electrodes 1 and 4
32—Electrode 1, current stimulation
34—Electrode 2, voltage sensing
36—Electrode 3, voltage sensing
38—Electrode 4, current stimulation
40—Resistance R2-3 represents the resistance from the blood volume in the heart
42—Low power amplifier
46—ADC with sampling synchronized to SinDAC outputs
48—Software algorithm to measure heart volume from electrical property measurements
50—Standard RV lead with three electrodes
52—Standard coronary sinus lead with two or four electrodes
54—Standard RA lead with two electrodes
58—Analog switch used to select multiple admittance vectors
61—Shocking coil on RV lead
62—Ring electrode on RV lead
63—Tip electrode on RV lead
64—Ring electrode on RV lead
65—Tip electrode on RV lead
66—Ring electrode on RV lead
67—Tip electrode on RV lead
110—The apparatus
112—The stimulator injects a safe current into the tissue
114—The sensor measures the response due to that stimulation
116—The signal processing, both analog and digital Description of Some Components 3—The tip of the cardiac pacing wire can have 2 or 4 electrodes, which make direct electrical connection to the myocardial tissue. The tips are designed so the pacing wire can be safely removed after the need for emergency cardiac pacing is no longer needed.

4—Cardiac pacing wire(s), which are externalized for post-surgical pacing. Examples include http://www.oscor.com/medical-devices/heartwires-TME64-66-224-226.html.

5—Current flows through the left ventricular blood pool. The resulting voltage generated is a function of the amount of blood in the left ventricle.

10—Some tips are designed for thin-wall tissue like atria, but are designed for thicker wall tissue like ventricles.

11—Two electrode configuration can be achieved with one pacing wire with two electrodes.

12—Four electrode configuration can be achieved with one pacing wire with four electrodes. An example of a quadripolar pacing wire is http://www.oscor.com/medical-devices/heartwires-TME227.html, incorporated by reference herein.

24—Wireless link can be a standard like Bluetooth Low Energy (BLE), IEEE802.11 Wifi, or a proprietary RF link depending on the application.

32—Examples of these electrodes include but are not limited to nonpolarized types such as Ag—AgCl, and polarized types such as silver, platinum and gold.

42—Low power amplifier

One example of a low power amplifier is the Texas Instruments INA322. This instrumentation amp runs with 490 µA of supply current, and has bandwidth of 2 MHz at a gain of 25.

58—Analog switch used to select one electrode for each of the four signals.

112—The stimulator generates a safe current that is injected into the tissue.

114—The sensor measures the voltage response due to that stimulation.

116—The signal processing removes motion artifacts and derives cardiac and pulmonary functions from the combination of stimulus and response.

In the operation of the invention, conductance measurements have been available as an invasive tool to detect instantaneous LV volume since 1981 [25, 26]. Conductance tetrapolar electrodes are usually placed on a catheter located within the heart chamber to determine instantaneous volume. Conductance systems inject current (5) into the tissue, and volume is determined from the returning voltage signal. Prior art shows how to separate the blood and muscle components from the combined voltage signal to determine LV preload from previously implanted AICD and bi-ventricular pacemakers.

Post-surgical management of patients undergoing heart surgery is a complex process involving multiple medications and fluid balance. To treat a post-surgical patient that is getting worse, the physician needs to know if the contractility is dropping, the SV is dropping, or neither is dropping. The availability of a real-time bed-side monitor of cardiac function will significantly improve patient care without increasing risks to the patient or altering standard surgical procedures.

There are several novel ideas employed in this bedside admittance device:

1) The method and apparatus uses pacing electrodes, EKG electrodes, or other electrodes with the low-power admittance technique to provide continuous and real-time measurements of cardiac function in post-surgical patients, including but not limited to heart rate, end diastolic heart volume, end systolic heart volume, change in heart volume, contractility, and/or stroke volume.
2) The method and apparatus uses novel signal processing to separate cardiac, respiratory, and motion signals. More specifically, the device may include an EKG channel to measure heart rate. The admittance signal is first synchronized to the heart rate, and then filtered so respiratory and motion artifacts are removed. These signal processing techniques will improve the effectiveness of data collected by a pacemaker from pacemaker leads 25.
3) The method and apparatus can spatially integrate measurements from two or more locations to give a more reliable cardiac signal. In particular, current can be injected into multiple locations simultaneously and voltage response can be measured from multiple locations simultaneously. This approach increases the cardiac signal, and hence improves signal to noise ratio.

Operation (how the Apparatus Works):

Prior art has defined the catheter and the relationship between electrical properties and heart physiology. Prior art also defined techniques that provide accurate measurements that are both low power and small in size. Prior art defines how the real and imaginary parts of the admittance measurement are combined to produce signals more sensitive to blood volume and less sensitive to muscle properties.

FIG. 1 presents the basic approach to the method and apparatus 110. The admittance device 1 is external to the body. Two or more electrodes 3 are temporarily attached to the myocardial tissue during open heart surgeries, and wires 4 are externalized. The purpose of these wires is to provide a means for emergency pacing during the post-operative monitoring period. The admittance device is either connected in parallel with the external pacemaker, or the measurement technique is added into the external pacemaker, extending the functionality of the external pacemaker to include these measurements of cardiac function.

Figure 2:
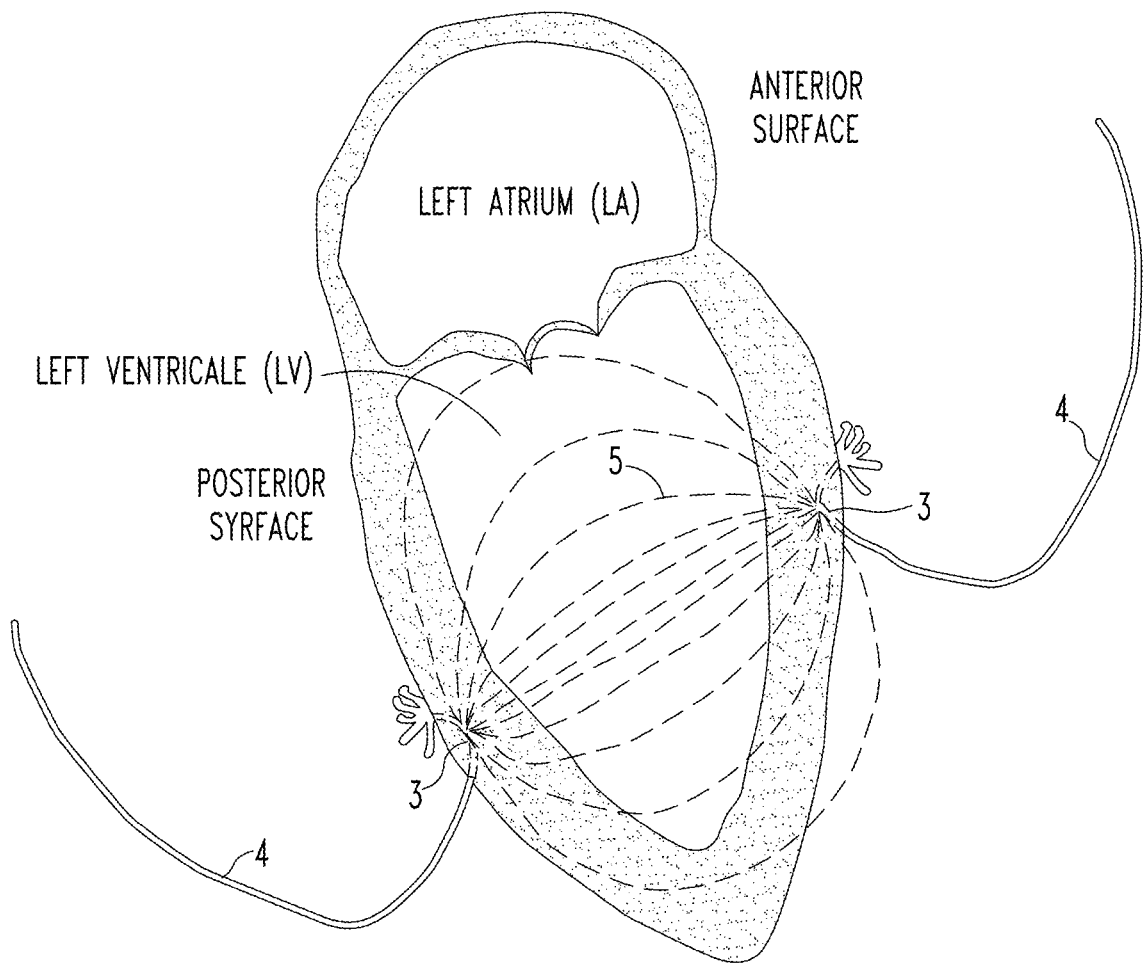
FIG. 2 shows a one pacing wire is placed on the anterior surface of the LV, and one pacing wire placed on the posterior surface of the LV. The principle of operation is to position the electrodes such that current flows across the blood in the ventricles. In this figure current flows across the left ventricle.
Figure 3A:
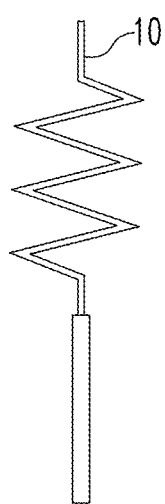
FIGS. 3A-3F show pacing wires come in different sizes and shapes. In each case, there is exposed metal that makes direct electrical contact with the myocardial tissue. Since these are temporary electrodes, there is a safe and effective means to remove the pacing wires.
Figure 3B:
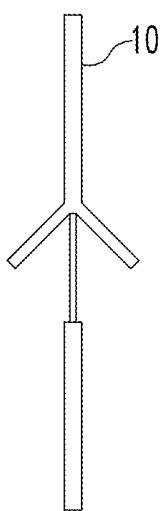
Figure 3C:
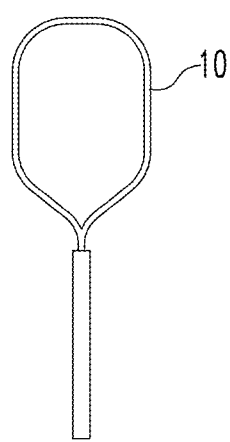
Figure 3D:
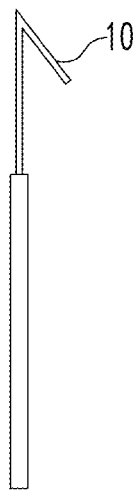
Figure 3E:
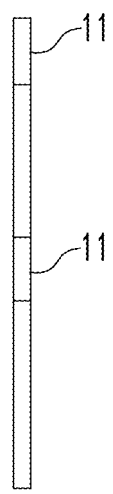
Figure 3F:
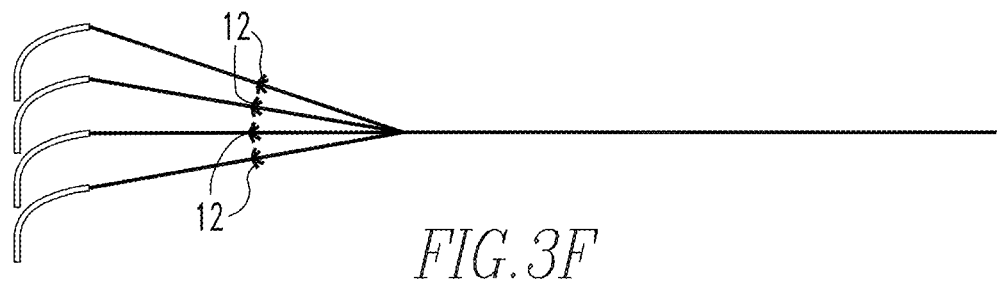

FIG. 2 shows injected current into the body at the current electrodes 3. AC current flows between the source and sink. The dotted lines 5 in FIG. 2 illustrate the direction and density of the current. Because blood has a five-fold higher electrical conductivity as compared to myocardial tissue, current will preferentially flow through the blood. Even if the source and sink exist on same surface of the heart, current will still flow through the blood because of this difference in electrical properties. The generated voltage measured at or near the current electrodes, is strongly dependent on the amount of blood that exists in the current path.

FIG. 3 illustrates various configurations of temporary pacing wires. Unipolar pacing wires 10 have one exposed electrode. Bipolar pacing wires 11 have two pacing wires, and quadripolar pacing wires 12 have four pacing wires. The application of this device and method will not require modification to these electrodes. There needs to be at least two electrodes in the myocardium, but the measurement works best when there are four or more electrodes. However, standard medical practice involves placing multiple electrodes onto the heart in order to maximum the ability to pace if an emergency occurs. The application of this apparatus 110 and method will not require modification to standard medical treatment.

Figure 4:
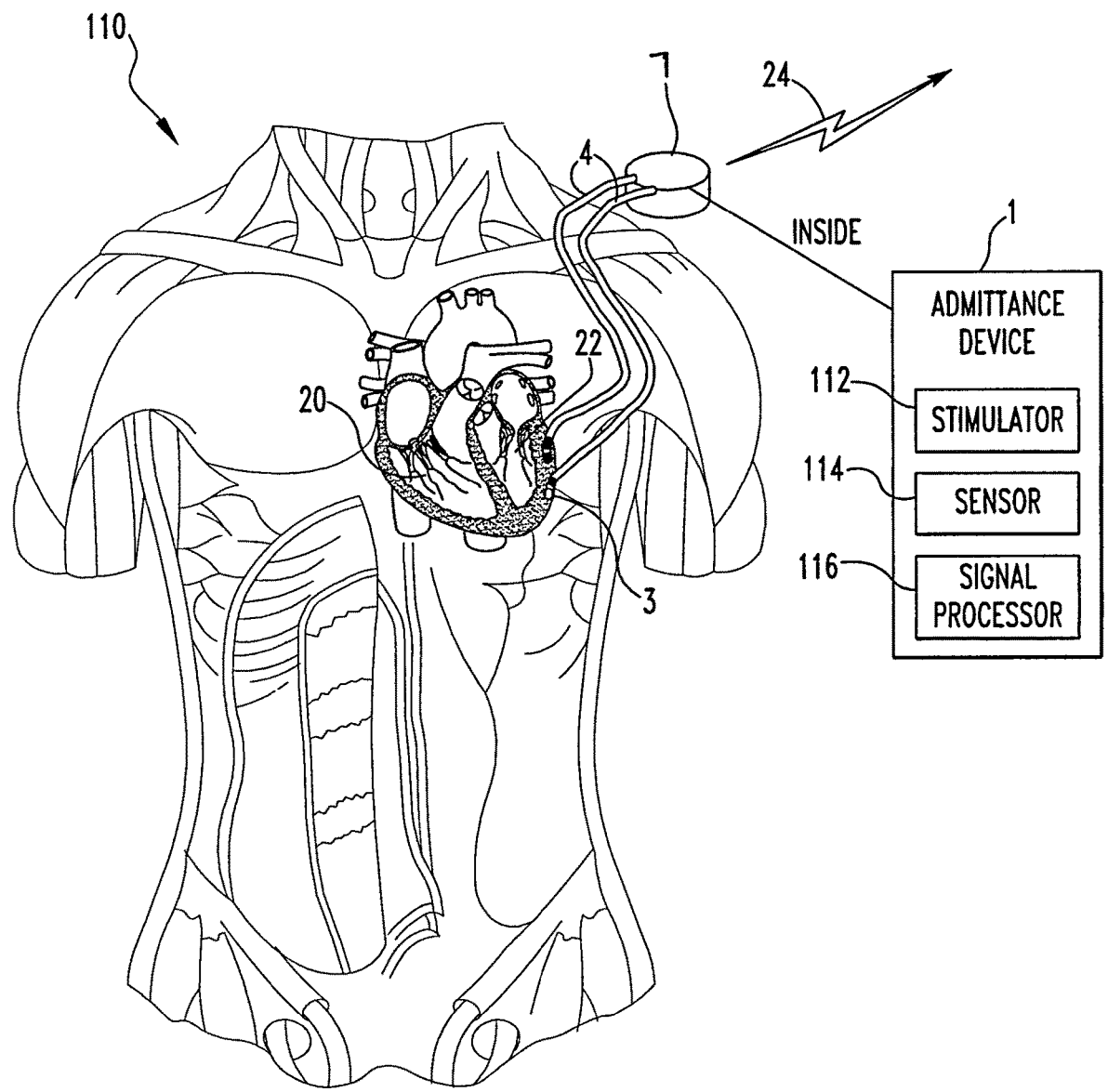
FIG. 4 shows two pacing wires with four electrodes are placed on the anterior surface of the left ventricle.
Figure 5:
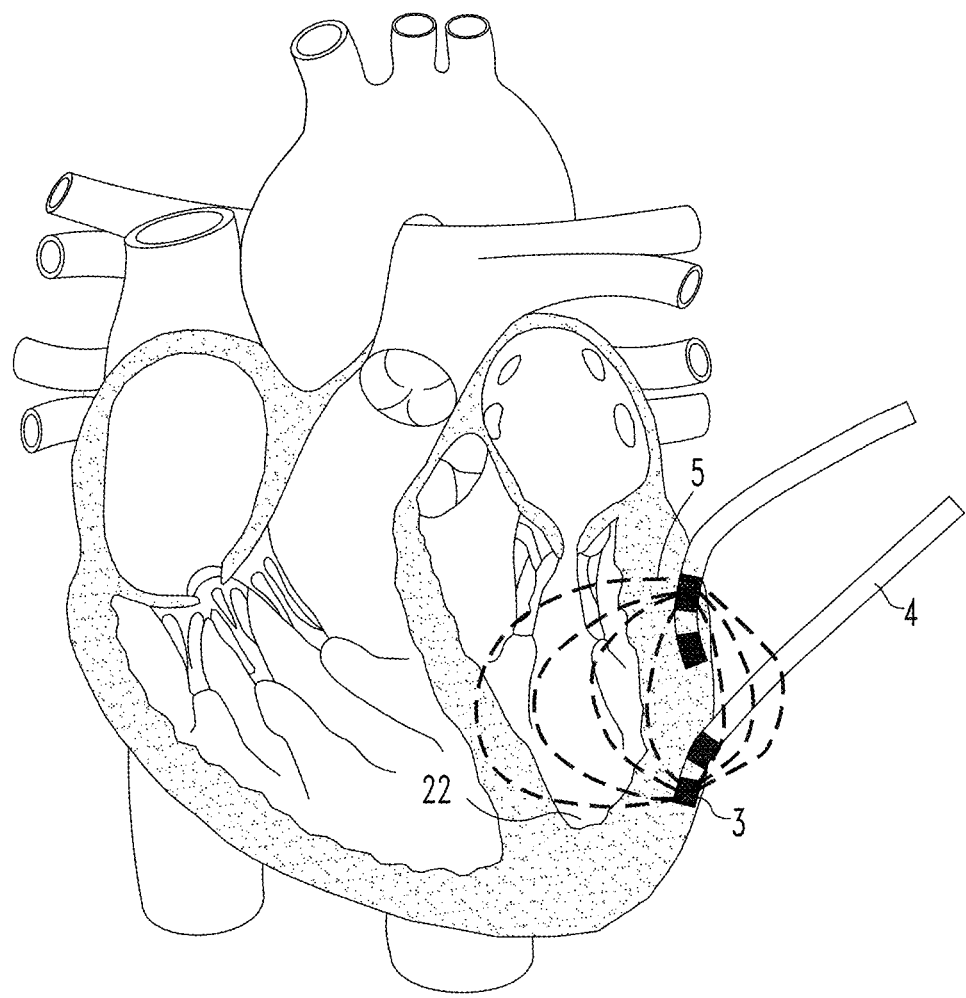
FIG. 5 shows a zoomed in view of four electrodes are placed on the anterior surface of the left ventricle and the resulting current lines.

FIG. 4 illustrates the method used when two bipolar pacing wires 11 are placed on the same side of the heart. In this figure, two electrodes will conduct current and the other two will measure the resulting voltage. FIG. 5 shows that because of the high electrical conductivity of blood, this configuration will still be sensitive to left ventricular (22) volume. If the electrodes were placed over the right ventricle (20), then the measurement would be sensitive to right ventricular volume. The device (1) consists of a stimulator 112, a sensor 114 and signal processing 116. A wireless link 24 provides two-way communication with a base-station or cell phone.

Figure 6:
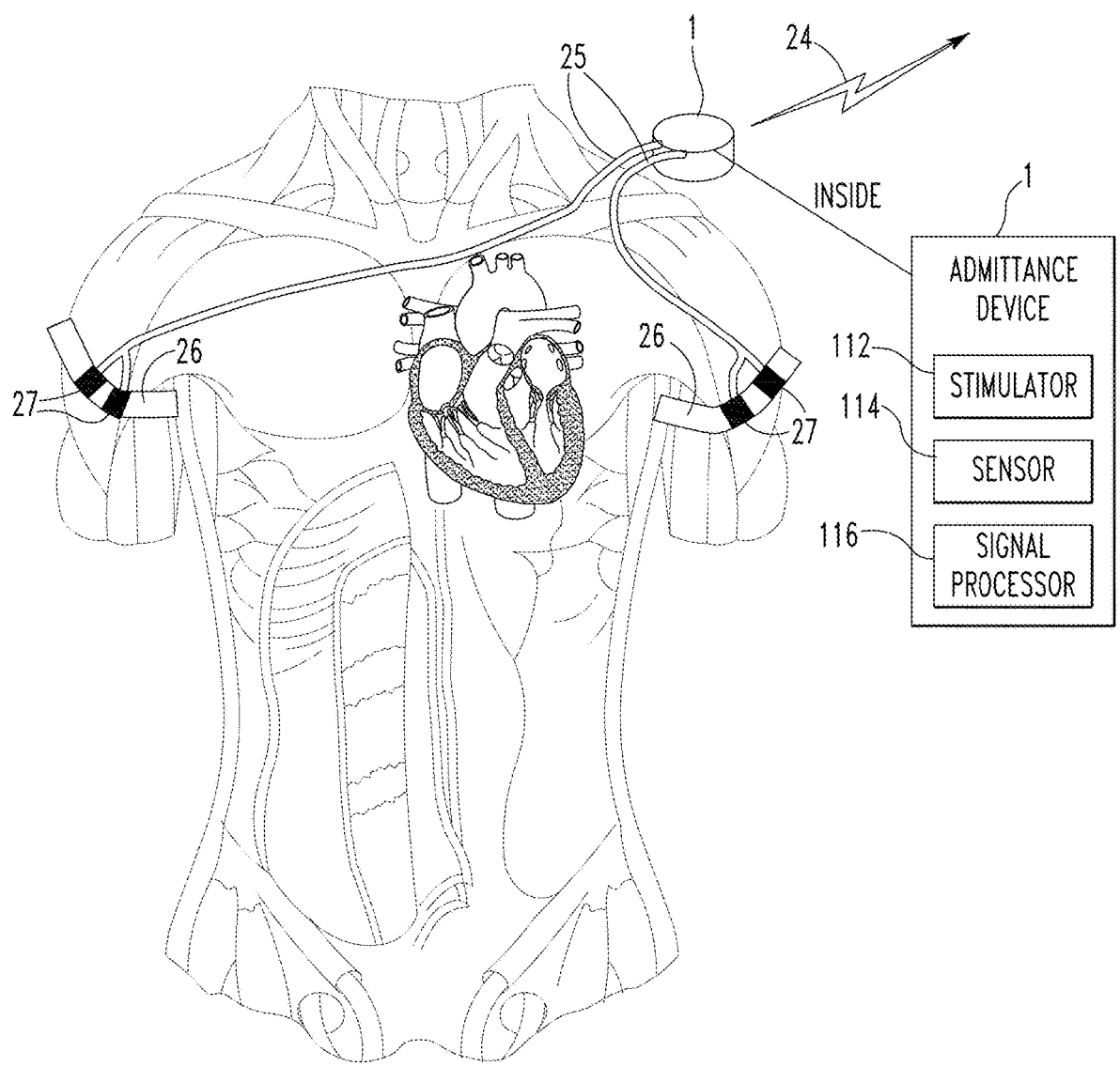
FIG. 6 shows two or more electrodes are placed left of the heart and two or more electrodes are placed right of the heart.
Figure 7:
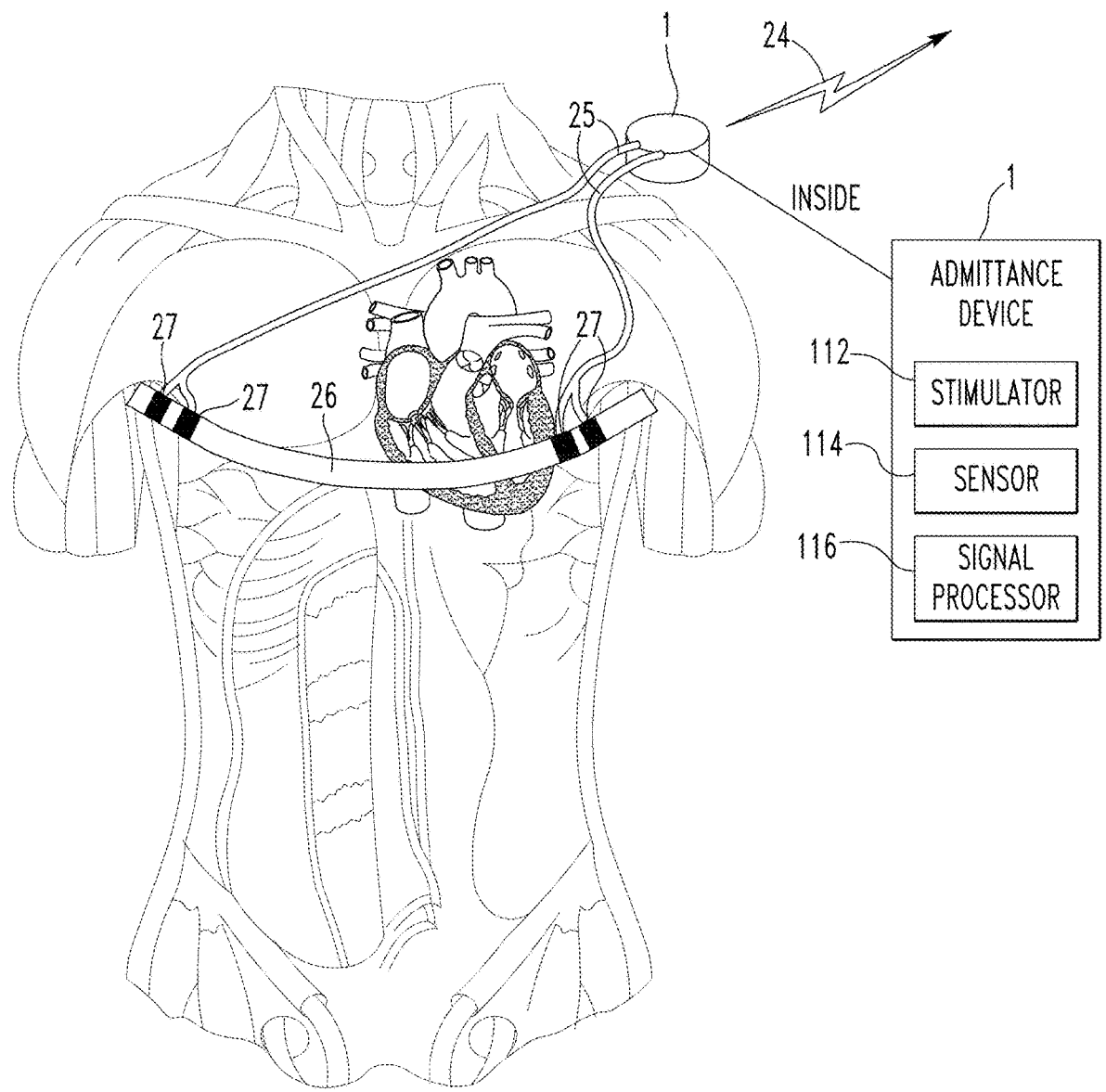
FIG. 7 shows two or more electrodes are placed anterior to the heart and two or more electrodes are placed posterior to the heart.

FIGS. 6 and 7 show the same method and apparatus 110 could be used to measure cardiac and pulmonary functions during exercise. The electrodes could be stitched into existing exercise apparel such as arm bands or shirts 26. In this case, the electrodes 27 are external to the body and will operate properly if electrical contact is maintained between the electrode and the skin. Again, because of the high electrical conductivity of blood, these configurations will generate signals sensitive to cardiac volumes. This configuration is also sensitive to pulmonary function.

FIG. 8 shows prior art of the device able to take accurate admittance data in real time and in a low power fashion. One or more SinDACs (28) generate a sine wave at a specified frequency. A low power circuit 30 is used to deliver the current to Electrode 1 32 and Electrode 4 38. The resulting voltage is generated across Electrode 2 (34) and Electrode 3 (36). The voltage response depends on blood volume in the heart, represented by R2-3 40 in the figure. A low power amplifier 42 and ADC 46 are used to collect data. Prior art described the method implemented in software (48) to derive complex measurements of admittance. FIG. 9 shows an example 20 kHz current wave applied to Electrodes 1 and 4. The frequency and amplitude of the current are selected to provide cardiac response without damaging or stimulating the heart.

FIGS. 10 and 11 show a prototype device and PCB consisting of a stimulator 112, a sensor 114, and signal processing 116. The RF antenna provides for wireless communication.

Figure 12:
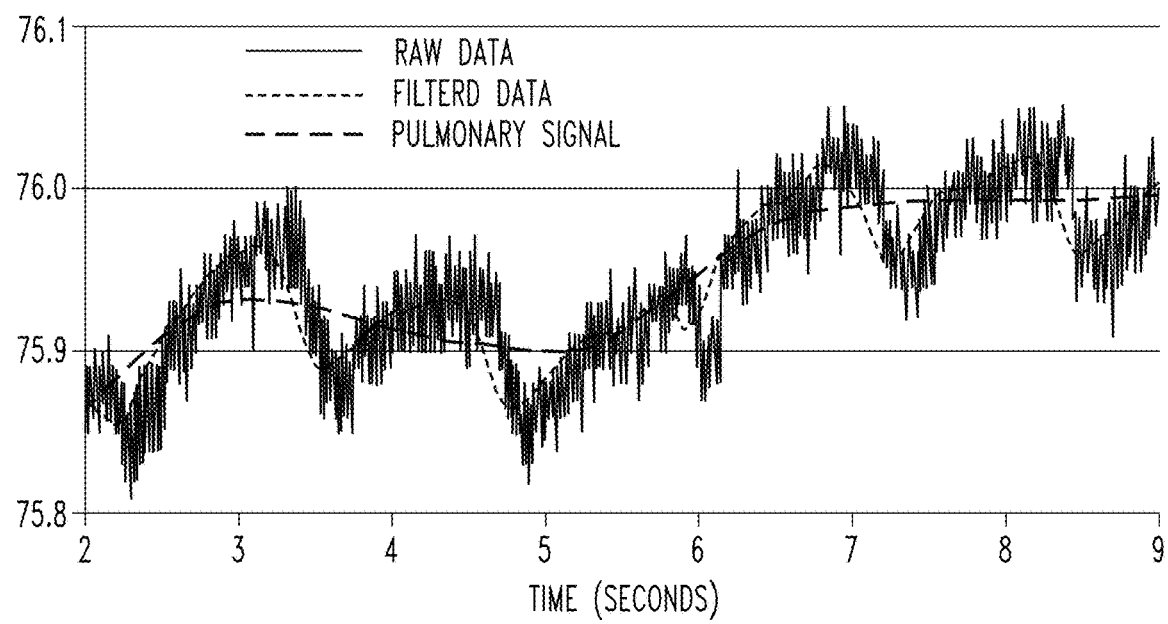
FIG. 12 shows measured and processed data showing the pulmonary and cardiac signals derived from the same data set.
Figure 12:
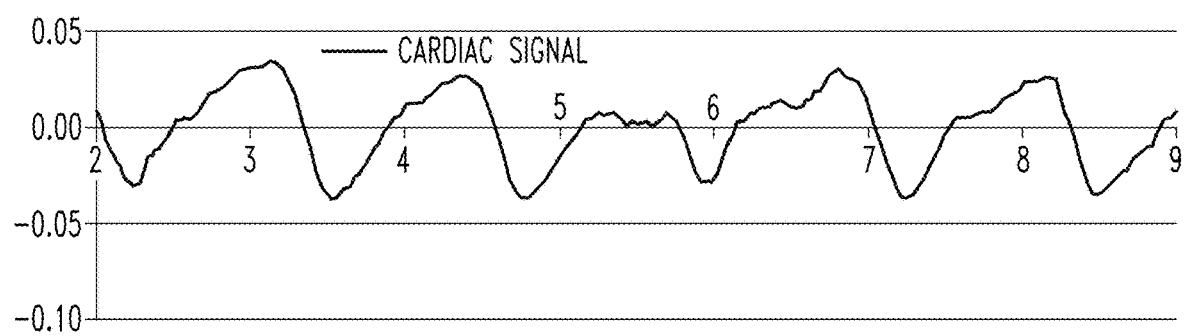
Figure 12:
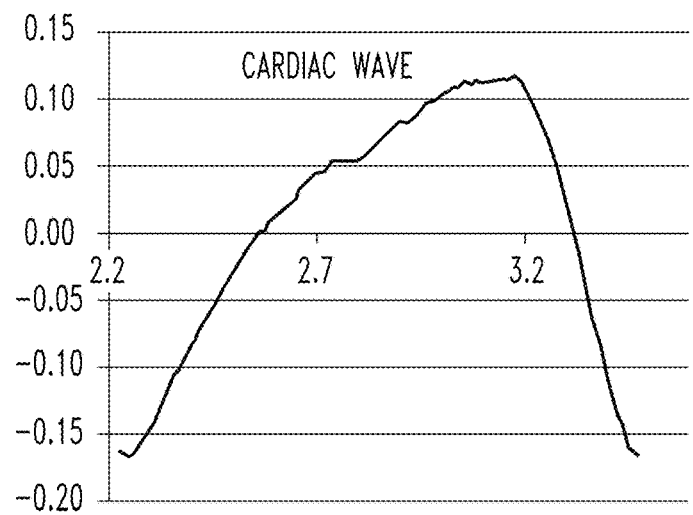
Figure 13:
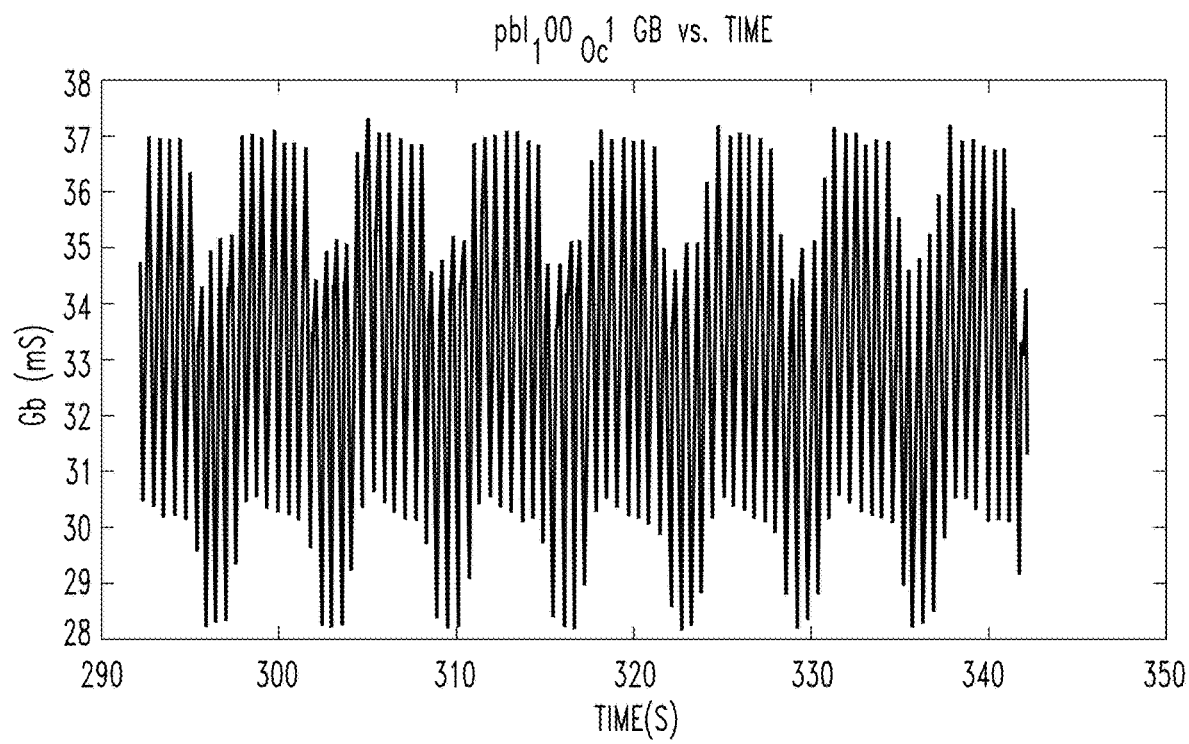
FIG. 13 shows admittance measured from electrodes placed in the right ventricle.
Figure 14:
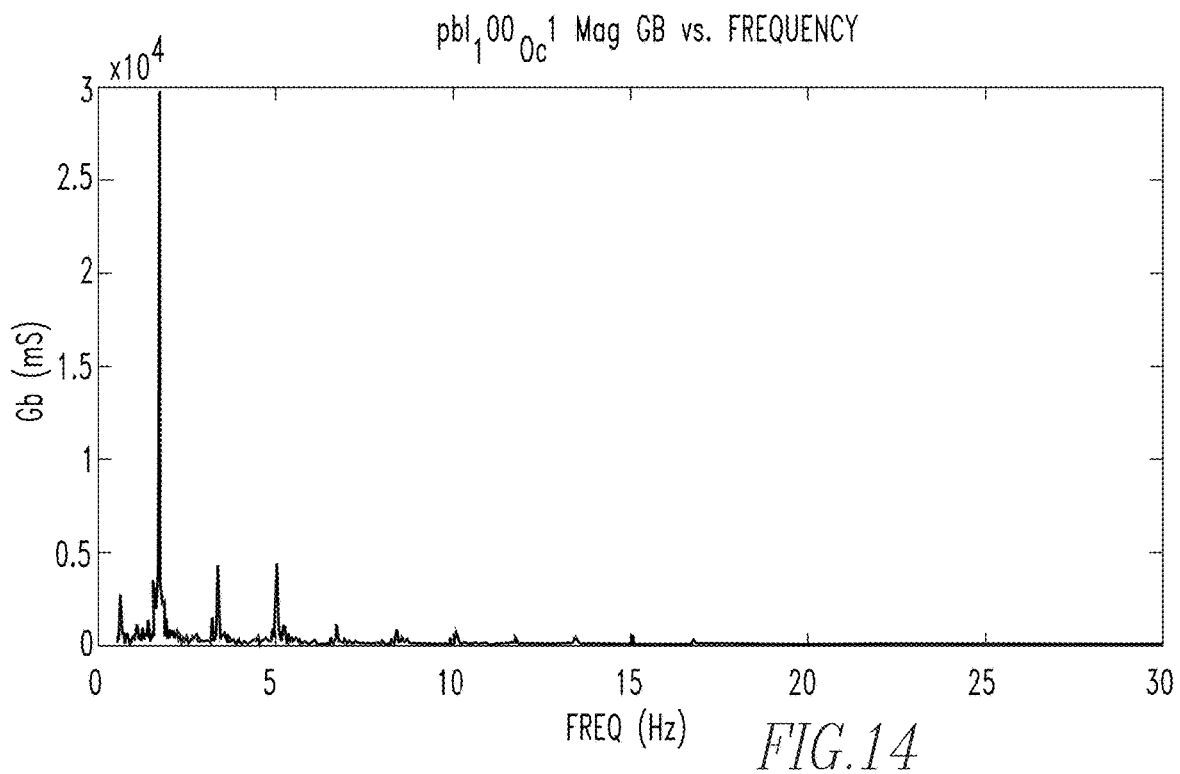
FIG. 14 shows FFT of the data from FIG. 13.
Figure 15:
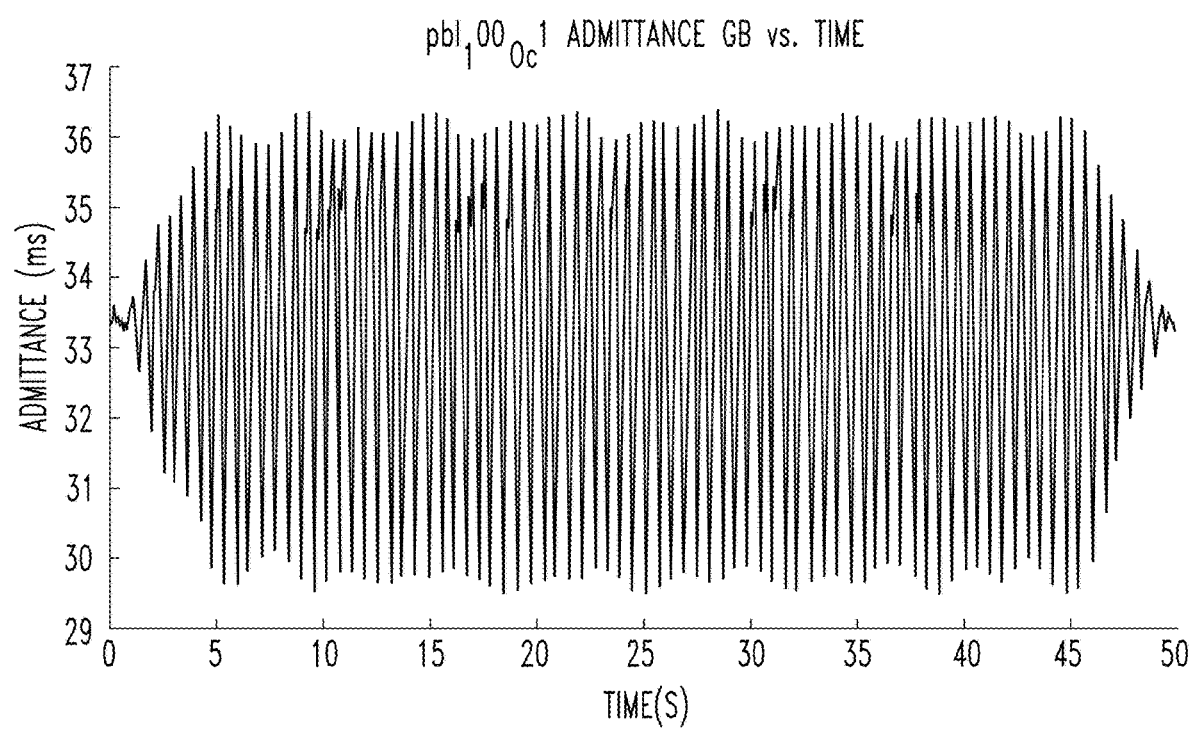
FIG. 15 shows inverse FFT of the data from FIG. 14 selecting the heart rate and the next to harmonics.

The basic approach to separating cardiac signals from the recorded data has six steps. FIG. 12 shows the large amount of noise existing in the raw data. The first step is to use the electrodes to measure EKG. The method and device will use EKG in a standard way to determine instantaneous heart rate. Let fHR be the heart rate in Hz. The second step is to collect admittance data over a T-sec second window. Shorter window times T provide for better data when the heart rate is fluctuating, while longer window times provide for improved SNR and increase the ability of the method to separate cardiac from pulmonary function. FIG. 13 shows a typical window. The third step is to perform a FFT of the windowed data. FIG. 14 shows the FFT of this same data. The fourth step is to select the following frequency components $$fHR \pm \Delta f, 2fHR \pm \Delta f, 3fHR \pm \Delta f, \ldots m*fHR \pm \Delta f,$$

where the number of harmonics, m, is selected on a case by case basis to improve SNR, and $\Delta f$ is selected to prevent the pulmonary signal from leaking into the cardiac measurements. In the data shown in FIG. 10, there is a strong fundamental at fHR and large harmonics at 2fHR and 3fHR. The fifth step is to perform an inverse FFT to recreate the cardiac signal. FIG. 15 shows the inverse FFT selecting just DC, fHR$\pm\Delta f$, 2fHR$\pm\Delta f$, and 3fHR$\pm\Delta f$. FIG. 15 shows the inverse FFT selecting just fHR$\pm\Delta f$, 2fHR$\pm\Delta f$, and 3fHR$\pm\Delta f$. The sixth step is to perform an RMS calculation on the cardiac signal as a measure of left ventricular stroke volume. The maximum signal is related to diastolic volume and the minimum signal is related to systolic value.

It should be noted that a single applied current source that has both a current lower than 100 micro-Amps ($\mu$A) RMS and a frequency above 1 kHz is considered "safe enough" under normal operating conditions.

As an example of the above, assume there is a patient who has a heart rate of 60 beats per minute (bpm). Taking a window of length T=50 seconds produces a graph of admittance vs. time similar to FIG. 13. The depicted graph in FIG. 13 takes advantage of the steady, non-fluctuating heart rate, by choosing a window which is long compared to the length of time the heart beats. fHR in this case is:

$$fHR = 60 \text{ bpm} * 1 \text{ minute}/60 \text{ seconds} = 1 \text{ Hz}.$$

This means the first three harmonics would rest at 1 Hz, 2 Hz, and 3 Hz. A $\Delta f$ value that could be chosen to isolate these harmonics (thereby cleaning up the signal), would be 0.25 Hz, so that the equation $$fHR \pm \Delta f, 2fHR * \Delta f, 3fHR \pm \Delta f, \ldots m*fHR \pm \Delta f,$$

simplifies to

1 Hz$\pm$0.25 Hz, 2 Hz$\pm$0.25 Hz, 3 Hz$\pm$0.25 Hz. It should be noted that in this example, there are three windows, but more windows could be added if desired, and fewer could be taken as well. When a very clean signal is present (no arrhythmia, strong components many harmonics away from the fundamental fHR, and T>>1/fHR) then it will be advantageous to take more. The rest of the frequencies in the frequency domain should then be set to zero.

At this point the inverse FFT will be performed, creating a time signal similar to the one in FIG. 15. In FIG. 15, the average maximum value is 36 mS, which corresponds to End Diastole. The minimum value is 29.5 mS on average, which corresponds to End Sysole.

To remove respiratory and motion artifacts, only knowledge of the frequency is necessary.

1. The frequency ranges of signals and noise can usually be determined by looking at the frequency spectrum after a Fourier transform of the time domain data. The heart normally beats in the 0.5-3 Hz range. Breaths normally occur at less than 0.5 Hz. Motion artifact is usually irregular, and not timed with the heartbeat. When "windowing" for the heart rate, (which is done at 1 Hz, 2 Hz, and 3 Hz in the example), all other noise can be filtered out by setting the non-cardiac signals frequencies to zero.

2. Independent verification of the frequency of the heart beat (for example, by ECG, which can be either external, or incorporated into the device) can be used to narrow the band width ($\Delta f$ in the example) to filter out more of the noise. The narrower the band $\Delta f$, the more unaffected by noise the signal will be.

In the data shown in FIG. 10, there is a strong fundamental at fHR and large harmonics at 2fHR and 3fHR, where fHR is about 1.8 Hz. By selecting 1.8, 3.6, and 5.4 Hz, and zeroing out the others, all of the respiratory and motion artifacts can be filtered out before taking the inverse FFT to extract the cardiac information. A similar methodology could be used to focus on respiratory signal, as evidenced by FIG. 16.

From the data, by placing the electrodes in, on, or across the heart, the apparatus is used to estimate heart rate, heart volume, stroke volume, change in heart volume, change in stroke volume, contractility, respiration rate and/or tidal volume."

To get more specific to how this would work in post-surgical applications, suppose a patient who has undergone an open heart surgery decompensates in the hospital the day after his/her surgery. The treating physician would have two potential treatments for this emergency situation that are opposite in nature. If the heart is weaker (low contractility, normal EDV, higher ESV than normal, lower SV than normal), then the treatment is to give a positive inotrope (this raises pressure, and blood flow in hearts that have enough blood). If instead the patient is decompensating because of low volume, (low EDV, but normal contractility, normal ESV, potentially lower SV) then the treatment is to give more fluids like IV saline. Choosing the wrong treatment can lead to further decompensation of the patient, and these decisions are often made somewhat uninformed in these situations, because of the lack of hemodynamic information that the apparatus of the present invention can now provide.

An alternate and less expensive method for making general admittance measurements does not require EKG measurement hardware. For this simpler approach, the admittance data is windowed, and the fHR value is selected as the frequency of the largest peak in the FFT data itself. FIG. 14 shows a strong signal at the heart rate.

A similar approach can be applied to derive pulmonary function. The frequency of respiration can be determined by observing the FFT data itself. Respiration is typically the largest peak in the FFT between DC and the heart rate. Let fresp be the frequency of respiration. To determine pulmonary function, the method selects just $$fresp \pm \Delta f$$

Figure 16:
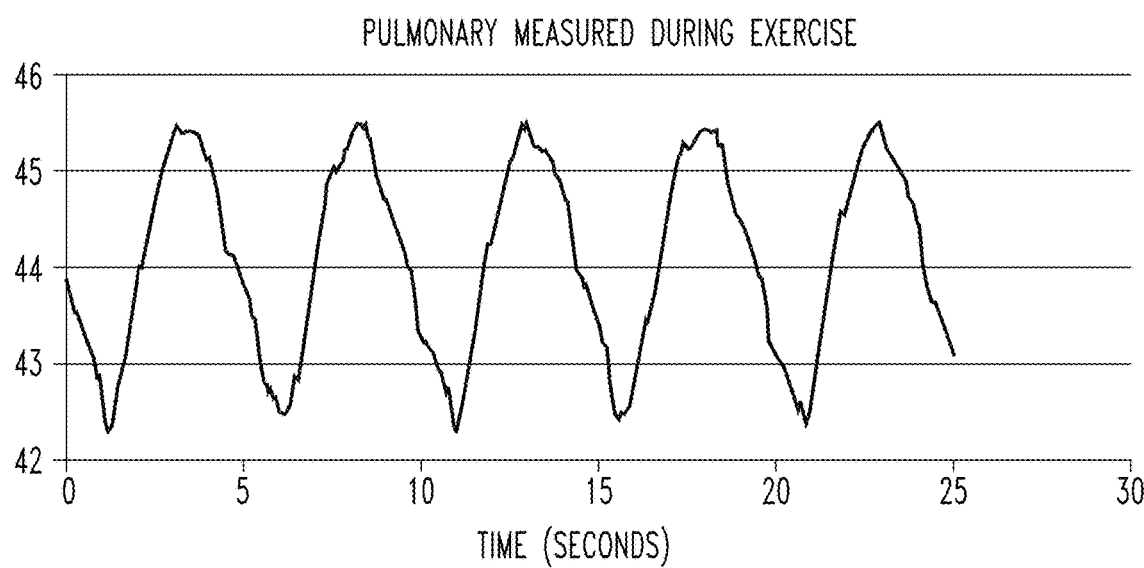
FIG. 16 shows pulmonary obtained during exercise.

FIG. 16 shows pulmonary function (lung volume) measured with this method measured during exercise. The RMS of the respiratory signal is linearly related to tidal volume.

A 3-axis accelerometer can be added to the device. Let ax, ay, and az be real-time measurements of acceleration. A non-directional calculation $$motion = ax^2 + ay^2 + az^2$$

provides a quantitative real-time measure of motion. During times of high motion, the number of harmonics m and the frequency band $\Delta f$ can be reduced so as to limit the amount of motion signal that spills into the cardiac data. The incorporation of acceleration information is particular important for measurements during exercise.

Due an FFT of motion and zero out the bins with large motion (blank if in cardiac bin, else zero)

Cardiac performance is often measured using the first derivative of the pressure tracing in a ventricle, to determine the maximum pressure change (maximum dP/dt) during isovolumic contraction (related to the contractility). In traditional conductance technology (not to be confused with complex admittance), there is no analogue to this measurement, because of the lack of an imaginary component (or, equivalently, phase angle). However, improvements have been made to the simple dP/dt max measurement that allow the calculation of contractility to be preload independent, by measuring the curve of the End-Systolic Pressure-Volume Relationship (ESPVR). While known methods of measuring load independent ESPVR are not widely performed in patients, it is possible using complex admittance, to measure a surrogate of dP/dt during isovolumic contraction due to the information that can be gleaned about the location of the myocardium. The phase signal, which can be separated out using the real and imaginary components of admittance, is related to the closeness of muscle to the voltage sensing electrodes. For example, as muscle tissue comes closer to the voltage sensing electrodes, the large permittivity causes a measurable phase shift. This real-time phase tracing can then be used to determine cardiac performance (a load-dependent measure of contractility), by taking the maximum of the first derivative during isovolumic contraction.

An alternate way of measuring contractility applies when two leads 25 are implanted in different locations in, or around the heart, where each lead contains a current source electrode (or sink electrode) and voltage electrode. In these cases, the distance between the two voltage electrodes dominates the signal, and the peak-to-peak signal approximates the "lead excursion". Lead excursion is the average change in distance between the leads 25, and is a direct surrogate of contractility, much like what would be measured using sonomicrometry. In practice, this involves taking the real part of the complex admittance (or complex impedance) signal, and measuring the cycle height (the maximum ReZ minus the minimum ReZ). This cycle height can be used as a direct measure of contractility.

A typical admittance signal is measured with four electrodes (tetrapolar) with two electrodes used to deliver current and two for measuring voltage. In many cases, this method can be extended to situations with more than four electrodes. FIG. 17 shows a typical scenario where a patient has three pacemaker leads 25 comprising 7 electrodes. The RV shocking lead 50 has three electrodes. The coronary sinus lead 52 has two electrodes. The RA pacing lead (54) has two electrodes. Some of the new coronary sinus leads 52 have four electrodes. It is not uncommon for patients to have more than four electrodes.

The method and apparatus 110 can deploy two approaches to this sensor-fusion. The first approach is illustrated in FIG. 18. The microcontroller (29) can control four banks of analog switches 58. There are four electrical signals in a tetrapolar admittance measurement: $+I_{out}$, $+V_{in}$, $-V_{in}$, and $-I_{out}$. In this method and device, the software can select any of the electrodes for each of the four signals. There are many combinations, but Table 1 lists four possible vectors. In each case the $+I_{out}$ electrode is located close to the $+V_{in}$ electrode and the $-I_{out}$ electrode is located close to the $-V_{in}$ electrode. The corresponding sensitive region will be the volume between $+V_{in}$ and $-V_{in}$ electrodes.

TABLE 1

Four possible admittance vectors, LV only

| Focus | $+I_{out}$ | $+V_{in}$ | $-V_{in}$ | $-I_{out}$ |
|---|---|---|---|---|
| Lower LV | RV tip (63) | RV ring (62) | CS ring (64) | CS tip (65) |
| Upper LV | RA ring (66) | RA tip (67) | CS tip (65) | CS ring (64) |
| Lower RV | RV tip (63) | RV ring (62) | RV coil (61) | RV coil (61) |
| Upper RV | RA tip (67) | RS ring (66) | RV ring (62) | RV tip (63) |
| LV only | CS tip | CS distal ring | CS mid ring | CS prox ring |

The software cycles through desirable vectors and then calculates admittance for each vector. Signal to noise ratio can be improved by adding admittance vectors in software.

The second approach is similar, except the averaging occurs in hardware. For one possible example, shown in FIG. 19, the $+I_{out}$ signal is connected to both RA tip and RV tip and the $-I_{out}$ signal is connected to CS tip. This creates a current field across the entire left ventricle. The voltages on RA ring and RV ring are averaged to create the $+V_{in}$ signal, and the $V_{in}$ signal is derived from CS ring. In this case, signal to noise ratio can be improved by adding admittance vectors in hardware. The circuit shown in FIG. 18 allows for this measurement because each of the switches 58 can be individually activated. By activating two or more switches at the same time, current can be directed out (in) multiple electrodes. Similarly, by activating multiple switches on the sensor allows the voltages from multiple electrodes to be averaged together.

LITERATURE CITED, ALL OF WHICH IS INCORPORATED BY REFERENCE HEREIN

1. Bleumink G S, Knetsch A M, Miriam C M, et al. Quantifying the heart failure epidemic: prevalence, incidence rate, lifetime risk and prognosis of heart failure. European Heart J 2005, 25, 1614-1619.
2. Moss A, Zareba W, Hall W, et al, for the Multicenter automatic defibrillator implantation trial II. Prophylactic implantation of a defibrillator in patients with myocardial infarction and reduced ejection fraction. NEJM 2002, 346, 877-883.
3. Barry G H, Lee K L, Mark D B, et al. Amiodarone or an implantable cardioverter-defibrillator for congestive heart failure. NEJM 2005, 35, 225-237.
4. Bristow M R, Saxon L A, Boehmer J, et al. Cardiac-resynchronization therapy with or without an implantable defibrillator in advanced chronic heart failure. NEJM 2004, 350, 2140-2150.
5. Cleland J F, Daubert J C, Erdmann E, et al. The effect of resynchronization on morbidity and mortality in heart failure. NEJM 2005, 352, 1539-1549.
6. Linde C, Abraham W T, Gold M R, et al. Randomized trial of cardiac resynchronization in mildly symptomatic heart failure patients and in asymptomatic patients with left ventricular dysfunction and previous heart failure symptoms. JACC 2008, 52, 1834-1843.
7. Vollmann D, Nägele H, Schauerte P, et al. Clinical utility of intrathoracic impedance monitoring to alert patients with an implanted device of deteriorating chronic heart failure. Eur Heart J 2007, 28, 1835-1840.
8. Yu C M, Wang Li, Chau E, et al. Intrathoracic impedance monitoring in patients with heart failure: correlation with fluid status and feasibility of early warning preceding hospitalization. Circulation 2005, 112, 841-848.
9. Luthje K, Drescher T, Zenker D, Vollmann D. Detection of heart failure decompensation using intrathoracic impedance monitoring by a triple-chamber implantable defibrillator. Heart Rhythm 2005, 2 (9), 997-999.
10. Wang L, Lahtinen S, Lentz L, et al. Feasibility of using an implantable system to measure thoracic congestion in an ambulatory chronic heart failure canine model. PACE 2005, 28 (5), 404-411.
11. Magalski A, Adamson P, Gadler F, et al. Continuous ambulatory right heart pressure measurements with an implantable hemodynamic monitor: a multicenter 12-month follow-up study of patients with chronic heart failure. J Cardiac Failure 2002, 8: 63-70.
12. Adamson P B, Magalski A, Braunschweig F, et al. Ongoing right ventricular hemodynamics in heart failure. JACC 2003, 41, 565-571.
13. Cleland J G, Coletta A P, Freemantle N, et al. Clinical trials updates from the ACC meeting. European J Heart Failure 2005, 7: 931-936.
14. Rozenman Y, Schwartz R S, Shah H, Parikh K H. Wireless acoustic communication with a miniature pressure sensor in the pulmonary artery for disease surveillance and therapy of patients with congestive heart failure. JACC 2007, 49, 784-789.
15. Abraham W T. Impedance beats weight in predicting heart failure events. Cardiology News 2009, 7 (10), 11 (abstract).
16. Ritzema J, Troughton R, Melton I, et al. Physician-directed patient self-management of left atrial pressure in advanced chronic heart failure. Circulation 2010, 121, 1086-1095.
17. Stahl C, Beierlein W, Walker T, et al. Intra-cardiac impedance monitors hemodynamic deterioration in a chronic heart failure pig model. J Cardiovasc Electrophysiol 2007, 18, 985-990.
18. Stahl C, Walker T, Straub A, et al. Assessing acute ventricular volume changes by intra-cardiac impedance in a chronic heart failure animal model. PACE 2009, 32, 1395-1401.
19. Feldman M D, Mao Y, Valvano J W, Pearce J A, Freeman G L. Development of a multifrequency conductance catheter-based system to determine L V function in mice. Am J Physiol, Heart Circ Physiol 2000, 279, H1411-H1420.
20. Wei C L, Valvano J W, Feldman M D, Pearce J A. Nonlinear conductance-volume relationship for murine conductance catheter measurement system. IEEE Trans Biomedical Engineering 2005, 52 (10), 1654-1661.
21. Reyes M, Steinhelper M E, Alvarez J A, et al, Feldman M D. Impact of physiologic variables and genetic background on myocardial frequency-resistivity relations in the intact beating murine heart. Am J Physiol, Heart Circ Physiol 2006, 291. H1659-H1669.
22. Wei C L, Valvano J W, Feldman M D, Nahrendorf M, Peshock R, Pearce J A. Volume catheter parallel conductance varies between end-systole and end-diastole. IEEE Trans Biomedical Engineering 2007, 54 (8), 1480-1489.
23. Raghavan K, Porterfield J E, Kottam Anil T, Feldman M D, Escobedo E, Valvano J W, Pearce J A. Electrical conductivity and permittivity of murine myocardium. IEEE Trans Biomedical Eng, 2009, 56 (8): 2044-2053.
24. Porterfield J E, Kottam A T, Raghavan K, Escobedo D, Trevino R J, Valvano J W, Pearce J A, Feldman M D. Dynamic correction for parallel conductance, G P, and gain factor, α, in invasive murine left ventricular volume measurements. Journal Applied Physiol, 2009, 107, 1693-1703.
25. Bann J, Jong T T, Kerkof P, et al. Continuous stroke volume and cardiac output from intraventricular dimensions, obtained with impedance catheter. Cardiovasc Res 1981, 15, 328-334.
26. Baan J, Van der Velde E T, de Bruin H O, et al. Continuous measurement of left ventricular volume in animals and humans by conductance catheter. Circulation 1984, 70, 812-823.
27. Stahl C, Beierlein W, Walker T, et al. Intra-cardiac impedance monitors hemodynamic deterioration in a chronic heart failure pig model. J Cardiovasc Electrophysiol 2007, 18, 985-990.
28. Stahl C, Walker T, Straub A, et al. Assessing acute ventricular volume changes by intra-cardiac impedance in a chronic heart failure animal model. PACE 2009, 32, 1395-1401.
29. Ring and Johnson counters are standard digital circuits. A ring counter is a sequence of flip flops placed in a ring, where the output of each flip-flop is the input to the next. A Johnson counter is a ring counter where one output is complemented before being connected to the next input. http://www.allaboutcircuits.com/vol_4/chpt_12/6.html or http://en.wikipedia.org/wiki/Counter.
30. Agilent Technologies, Agilent Impedance Measurement Handbook, 4th edition, http://cp.literature.agilent.com/litweb/pdf/5950-3000.pdf
31. Porterfield J, Larson E, Jenkins J, Escobedo D, Valvano J, Pearce J, and Feldman M, Left Ventricular Epicardial Admittance Measurement for Detection of Acute L V Dilation, Journal of Applied Physiology (JAPPL-01047-2010R1), 2010.
32. Uemura K, Kawada T, Sugimachi M, Zheng C, Kashihara K, Sato T and Sunagawa K 2004 A self-calibrating telemetry system for measurement of ventricular pressure-volume relations in conscious, freely moving rats Am. J. Physiol. Heart Circ. Physiol. 287 H2906-H2913.
33. Raghavan K, Design of a wireless bio-telemetric device for measurement of left ventricular pressure-volume loops using the admittance technique in conscious, ambulatory rats, PhD dissertation, May 2009.
34. Raghavan K, Feldman M, Porterfield J, Larson E, Jenkins J, Escobedo D, Pearce J, and Valvano J, Bio-telemetric device for measurement of left ventricular pressure-volume loops using the admittance technique in conscious, ambulatory rats, in review, Physiological Measurements.
35. U.S. patent application Ser. No. 13/373,850 filed Dec. 2, 2011.
36. U.S. Pat. No. 9,295,404 issued on Mar. 29, 2016.
37. U.S. patent application Ser. No. 13/648,725 filed Oct. 10, 2012.
38. U.S. patent application Ser. No. 12/924,195 filed Sep. 22, 2010.
39. U.S. Pat. No. 8,706,219 issued on Apr. 22, 2014.
40. U.S. Pat. No. 7,925,335
41. U.S. Pat. No. 6,494,832
42. U.S. patent application Ser. No. 12/657,832
43. U.S. patent application Ser. No. 12/086,040

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for monitoring a patient post operation comprising: a computer disposed external to the patient; a stimulator adjacent the computer and external to the patient for producing sampling electrical signals for diagnostic purposes; and electrically conducting leads in communication with the computer and the stimulator which are adapted to extend outside the patient from inside the patient and be safely removed without further injury from the patient when post operation ends, the leads having electrodes adapted to communicate with a heart of the patient and apply the electrical signals to the heart, the electrodes providing admittance based cardiac signals to the computer in response to the electrical signals so the computer determines in real time and continuously using admittance at least one of heart volume, end diastolic heart volume, end systolic heart volume, stroke volume, change in heart volume, change in stroke volume, contractility, respiration rate or tidal volume regarding the patient, the computer separates respiratory and motion components to isolate the admittance based cardiac signals, the computer synchronizing the electrical signals to a heart rate of the patient.

2. The apparatus of claim 1 wherein the computer and the stimulator are disposed in and part of an external pacemaker external to the patient which can electrically stimulate the electrodes and pace the heart.

3. The apparatus of claim 2 wherein the leads are pacing leads with the electrodes that pace the heart from the pacemaker or leads with the electrodes placed on one or more chest tubes which extend from the patient and are disposed adjacent the heart of the patient.

4. The apparatus of claim 3 wherein the pacing leads are either unipolar pacing wires each having one of electrode, bipolar pacing wires having two pacing wires, or quadrupole pacing wires each having four pacing wires.

5. The apparatus of claim 4 wherein there are at least 4 electrodes where a first two of the electrodes conduct current and a second two electrodes receive voltage signals resulting from the current from the first two electrodes.

6. The apparatus of claim 5 including a SinDac disposed in the pacemaker which generates a sine wave at a specific frequency in regard to the current.

7. The apparatus of claim 6 including a sensor, a signal processor of the computer and low-power circuit, where an average current to operate the sensor, stimulator and signal processor is less than 14 mA, the sensor and stimulator and signal processor comprise the low-power circuit, and the low-power circuit is used to deliver the current to the current electrodes.

8. The apparatus of claim 7 including a low-power amplifier and ADC which are used to collect the voltage signals for the computer to use for analysis.

9. A method for monitoring a patient post operation comprising the steps of: providing admittance based cardiac signals to a computer disposed external to the patient from electrically conducting leads in communication with the computer which extend outside the patient from inside the patient, the leads having a plurality of electrodes adapted to contact a heart of the patient and be safely removed from the patient when post operation ends; the computer separating respiratory and motion components from the admittance based cardiac signals to isolate the cardiac signals; the computer synchronizing electrical signals to a heart rate of the patient, the electrical signals are sampling electrical signals for diagnostic purposes; determining with the computer from the cardiac signals in real time and continuously using admittance at least one of heart volume, end diastolic heart volume, end systolic heart volume, stroke volume, change in heart volume, change in stroke volume, contractility, respiration rate or tidal volume regarding the patient; and safely removing the leads without further injury and the electrodes from the patient when post operation is over.

10. The method of claim 9 including the steps of placing the plurality of electrodes in contact with the heart;
   externalizing electrical leads extending from the electrodes with respect to the patient; and
   connecting the leads to the computer.

11. The method of claim 10 including the step of providing current signals from a stimulator adjacent to the computer to the electrodes to generate the cardiac signals.

12. The method of claim 11 wherein the computer and the stimulator are disposed in and part of an external pacemaker external to the patient which can electrically stimulate the electrodes and pace the heart.

13. The method of claim 12 wherein the leads are pacing leads with the electrodes that pace the heart from the pacemaker.

14. The method of claim 13 wherein there are at least 4 electrodes, and including the steps of a first two of the electrodes conducting current and a second two electrodes receiving voltage resulting from the current from the first two electrodes.

15. The method of claim 14 including the step of a SinDac disposed in the pacemaker generating a sine wave at a specific frequency in regard to the current.

* * * * *